United States Patent
Burke

(10) Patent No.: US 8,560,045 B2
(45) Date of Patent: Oct. 15, 2013

(54) MEASUREMENT FOR AUTONOMIC FUNCTION

(71) Applicants: Richard Gearhart, Chatham, NJ (US); Biographs LLC, Commack, NY (US)

(72) Inventor: John Burke, Summit, NJ (US)

(73) Assignee: Biographs, LLC, Commack, NY (US)

( * ) Notice: Subject to any disclaimer, the term of this patent is extended or adjusted under 35 U.S.C. 154(b) by 0 days.

(21) Appl. No.: 13/633,514

(22) Filed: Oct. 2, 2012

(65) Prior Publication Data

US 2013/0035580 A1 Feb. 7, 2013

Related U.S. Application Data

(63) Continuation of application No. 13/247,002, filed on Sep. 28, 2011, now abandoned, which is a continuation of application No. 11/891,890, filed on Aug. 14, 2007, now abandoned.

(60) Provisional application No. 60/837,658, filed on Aug. 15, 2006.

(51) Int. Cl.
*A61B 5/04* (2006.01)

(52) U.S. Cl.
USPC ............ 600/391; 600/396; 600/382; 600/557

(58) Field of Classification Search
USPC ................. 600/391, 395, 396, 382, 301, 557; 128/898
See application file for complete search history.

(56) References Cited

U.S. PATENT DOCUMENTS

| 5,447,947 | A | * | 9/1995 | Campbell | 514/392 |
|---|---|---|---|---|---|
| 5,501,230 | A | | 3/1996 | Laribiere | |
| 6,347,238 | B1 | * | 2/2002 | Levengood et al. | 600/372 |
| 6,571,124 | B1 | * | 5/2003 | Storm | 600/547 |
| 6,950,688 | B2 | | 9/2005 | Axelgaard et al. | |
| 2002/0107434 | A1 | * | 8/2002 | Lange et al. | 600/301 |
| 2006/0052720 | A1 | * | 3/2006 | Ross et al. | 600/554 |

OTHER PUBLICATIONS

Clochesy JM, Ripich S, Hollowood D, Travis LL. "Offset Potential of Commercial ECG Electrodes" Heart Lung 22(6):490-93 (1993).*
PCTUS/2007/017984; Jan. 22, 2008; Biographs, LLC; PCT Written Opinion.
PCT/US2007/017984; Jan. 22, 2008; Biographs, LLC; Int'l Search Report.
PCT/US2007/017984; Feb. 26, 2009; Biographs, LLC; IB Patentability Report.
Clochesy, John, M. et al; Offset Potential of commercial ECG electrodes; Heart & Lung; Nov./Dec. 1993; pp. 490-493.

* cited by examiner

*Primary Examiner* — Lee S Cohen
*Assistant Examiner* — Erin M Cardinal
(74) *Attorney, Agent, or Firm* — Gearhart Law, LLC

(57) ABSTRACT

The present invention is an article of manufacture and method for using same, comprising at least two self adhesive sensors having a paired offset potential of consistently below about +/−1.0 mV; and a data gathering device connected to the sensors capable of measuring the voltage difference between the sensors. The sensors preferably are AgCl coated Silver.

20 Claims, 30 Drawing Sheets

LCD Display reading is in positive mV

MEASUREMENT FOR AUTONOMIC FUNCTION

PRIORITY CLAIM

This application is a continuing application of U.S. application Ser. No. 13/247,002, which was filed Sep. 28, 2011 and was a continuing application of Ser. No. 11/891,890 filed Aug. 14, 2007 and claimed priority of U.S. provisional application No. 60/837,658 filed Aug. 15, 2006; all of which are incorporated herein by reference.

FIELD OF THE INVENTION

The invention relates to methods of detecting and quantifying nociception and pain, and devices and components related thereto.

BACKGROUND OF THE INVENTION

The autonomic nervous system (ANS) governs the functioning of numerous organs in the body of humans and other mammals. Yet there exists no quick, simple, inexpensive, or reliable test to measure the full range of autonomic function in an individual, nor its current state.

The two major components of the ANS are the sympathetic nervous system (SNS) and the parasympathetic nervous system (PNS). Nerves from both usually innervate the organs they control. Thus organ performance is the result of the interplay of both PNS and SNS. A measure of either SNS or PNS is not very useful in assessing the condition of the subject. For example, a subject may have high PNS tone without being relaxed because its effects are being offset by high SNS tone. Heart rate, for example, is determined by interplay between PNS and SNS. Both nerves innervate and affect our hearts. When a subject's PNS vagal nerves to the heart are cut, its heart rate rises and remains elevated.

A novel method is described herein to measure the moment-to-moment relative dominance of PNS tone (sometimes also referred to as vagal tone) and SNS tone. The method is inexpensive, easily understood, consistent, reliable, as well as simple and quick to administer. It is completely passive and requires no voltage to be administered to the subject, thus eliminating the possibility of side effects from the resultant current. It works well on both humans and animals.

The method gives a distinctive, "signature" reading for subjects experiencing any moderate to severe pain that has lasted for more than a few minutes, both in humans and other mammals. Therefore, it provides a previously non-existent, objective description of pain. Currently, all pain is now measured by asking the subject questions about their pain (i.e., "On a scale of 0-10, how would you rate your pain?"). This is clearly subjective. Non-verbal patients cannot be evaluated by these methods. Thus health care providers are at a loss to measure pain in young children, advanced dementia adults, some stroke victims and intubated patients, as well as the rest of the animal kingdom. Prey species of animals (including horses and sheep) pose a particular challenge because they are genetically programmed to mask their pain so as not to become the primary target of a predator. Even expensive thoroughbred racehorses are often the subject of vigorous debate by their caretakers regarding their pain status. Furthermore, a reliable and consistent objective measure of pain would prove useful to doctors who suspect the patient is exaggerating or imagining his or her pain, as well as to insurers who suspect malingering.

The method described herein works by recording a measurable physiological correlate of ANS changes, namely the difference in electrical potential between two sensors placed on the skin. Similar to the Tarchinoff voltage measure of electrophysiology, it differs by sensing between sites of similar instead of high to low sweat gland densities. Skin is innervated by nerves from both the SNS and PNS, which, respectively, increase and decrease physiological rates in tissue and organs throughout the body. These nerves are distributed relatively symmetrically throughout the body but are not always activated in a symmetrical manner. With pain, for example, persistent pain from anywhere in the body of moderate to severe intensity begins to raise blood pressure (BP). This activates the baroreceptors in the carotid sinus artery. They trigger an increase in PNS (vagal) tone in an attempt to stop the BP increase and restore homeostasis. In addition, this process triggers the release of endorphins, the body's own, natural opioids, which provide partial pain relief. This process is part of what is known as Descending Nociceptive Inhibitory Control, or DNIC. This response is mediated primarily by the right cardiac vagal (PNS) nerve, not the left one. This nerve branches off and innervates other tissue along the way. The result is slightly slower physiology on the right side of the body. It has now been found that this includes the two-skin-site voltage difference effect. Accordingly, the voltage sensed on the right side of the body, with respect to the left, drops as PNS tone rises through increased activation of the right cardiac vagal nerve.

PRIOR ART

Most Galvanic Skin Reflex measurement has been done by sensing the Fere effect, so named after its discoverer. This is the change in the skin's ability to conduct electrical current due to sweat gland activity. The reason for this method has been due partly to the relative ease, reliability, and consistency of measurements. This is due to the relatively large applied voltages used to measure the Fere effect, in contrast to the small, natural, body voltages of the Tarchinoff aspect of the GSR. In the case of the present invention, the magnitude of the voltage difference between the right and left sites on the body, is often smaller than the offset voltages of sensors which have been standard in the industry. Data gathered with high offset sensors would lead to inconsistent measurements and the conclusion that there was no useful information to be obtained this way. The invention described herein overcomes these deficiencies of the prior art methods.

Two posters have been presented at medical conferences showing anecdotal reports of such ANS shifts reflected in skin potential. (Ngeow, et al, Aug. 21-26, 2005), (D'Angelo, May 2006). This previous work did not use sensors which had been selected for their low offset potentials. The practitioners presenting these posters had been unaware of the role of offset potentials in these types of measurements, and it was not discussed in their posters. The form of sensor used to obtain the data presented in the posters has produced a wide and changing variety of offset potentials due to a combination of factors. One was a lack of consistency in manufacture. Still another was a lack of consistency in use. These sensors were of a cup style which required the examiner to fill the cups above the Ag/AgCl coated sensor surface to the brim of the cup with conductive gel. If the examiner fails to place the adhesive collar with its hole directly above the cup, part of the collar will cover some of the electrode gel, blocking its area of contact with the skin. This may produce a smaller signal coupled to the system load resistor. In addition, if the examiner fails to fill one of the cups completely to the brim, this may introduce a difference between the area of contact of the two recording electrodes that also may produce a smaller coupled signal. Occasionally, good readings can be taken, such as those selected for the posters, but they cannot be obtained consistently with the type of sensor methodology shown in the posters even with trained personnel in the time conscious environment of a clinical setting. The proposed method solves that by using pre-applied gel that has been spread evenly on each electrode during manufacture, producing much more consistent readings.

The present low offset voltage sensors invention can be used to track the progress of an individual during a series of treatments or during healing, due to consistent readings obtained by minute and consistent offset potentials. This cannot be said of most other types of electrodes.

Most prior work involving the use of measuring sensors on the skin in order to chart autonomic changes has been Galvanic Skin Resistance Work. This also uses electrodes on the hands, but the purpose and approach is of an entirely different type. In GSRes an external voltage is applied to the subject's skin through a pair of sensors and the OSRes unit measures the current.

Levengood and Gedye in U.S. Pat. No. 6,347,238 utilize some of the same hardware as the disclosed invention but their method has great limitations. Levengood teaches electrodes against which the hand must be pressed neither of which is self-adhesive and both of which must be pressed against the hand or body by the physical force of tester or subject. Since the magnitude of the coupled resistance loaded signal is affected by the area of contact, even very slight variations in pressure produce artifacts, namely variations in the recording. If skin surface contact resistances of the sensor pair, in some manner, tap into a bulk, internal, electrical field gradient, a voltage polarity reversal may even be brought about by a difference in physical force being applied to the left versus right sensor. The self-adhesive sensor employed in the present invention eliminates this deficiency. Levengood's method is further limited by its use of solid metals. Virtually all solid metals form a "half-cell" potential when they are in contact with a saline solution such as the subject's perspiration. This well known electrochemical effect need not be further elucidated. The absolute and imbalance magnitudes of the half-cells for aluminum, the metal specified in Levengood, are amongst the largest for solid metals. This artifact can overshadow the small signals being sought in the two-sensor site voltage measure. At a minimum, it will affect the numeric reading of the site to site voltage. AgCl coated Ag sensors of the type employed in the present invention minimize this effect. Such low offset sensors are not taught by Levengood.

Unlike prior art that deals primarily with the Fere effect and involves active addition of extraneous electrical current to the skin, the present invention, like Levengood, measures only the two site voltage measure. Leavengood does not teach the involvement of the ANS. Accordingly, the occasional false positive cannot be spotted. Occasionally a subject produces a positive reading despite being in moderate to severe pain. If ANS indictors such as Heart Rate and Diastolic Blood Pressure are over 95, the examiner can take into account that SNS tone is obviously extremely high at the moment and therefore the reading is unreliable. A chronic pain patient with pain of 7 on the 0-10 VAS scale could still produce a positive reading under these conditions. Thus the other cited prior art does not teach the disclosed method. None of the cited prior art deals with offset potentials of the sensors used. Without consideration of offset potentials, the weak two site voltage difference cannot be measured accurately. Even some commercial Ag/AgCl sensors possess offset potentials sufficient to seriously affect the voltage readings of the present method. However, by utilizing low offset potential electrodes (i.e. below 1.0 mV as in the disclosed system, and the lower the offset potential the better) as described in more detail herein below, the voltage difference can be measured with consistent accuracy. Selected low offset potential sensors were not taught in the prior art.

SUMMARY OF THE INVENTION

The present invention is an article of manufacture and method for using same, comprising at least two electrodes or "sensors" having an offset potential of below about +/−1.0 mV; and a data gathering device connected to the sensors capable of measuring the voltage differential between the electrodes. The sensors preferably are AgCl coated Silver.

It is an object of the invention to teach a device capable of measuring pain in a subject.

It is also an object of the invention to detect changes in the ANS.

It is a further object of the invention to teach a device capable of measuring pain that uses low offset potential sensors.

It is another object of the invention to teach a device that senses voltage and does not pass a significant, exploratory current through the subject.

It is yet another object of the invention to teach a pain measuring device that utilizes AgCl coated Ag sensors.

It is also an object of the invention to teach the use of a low offset electrode in a pain measuring device.

It is yet a further object of the invention to teach a device and method which allows consistent quantifiable measurement of pain.

DESCRIPTION OF THE PREFERRED EMBODIMENTS

Figure 1A:
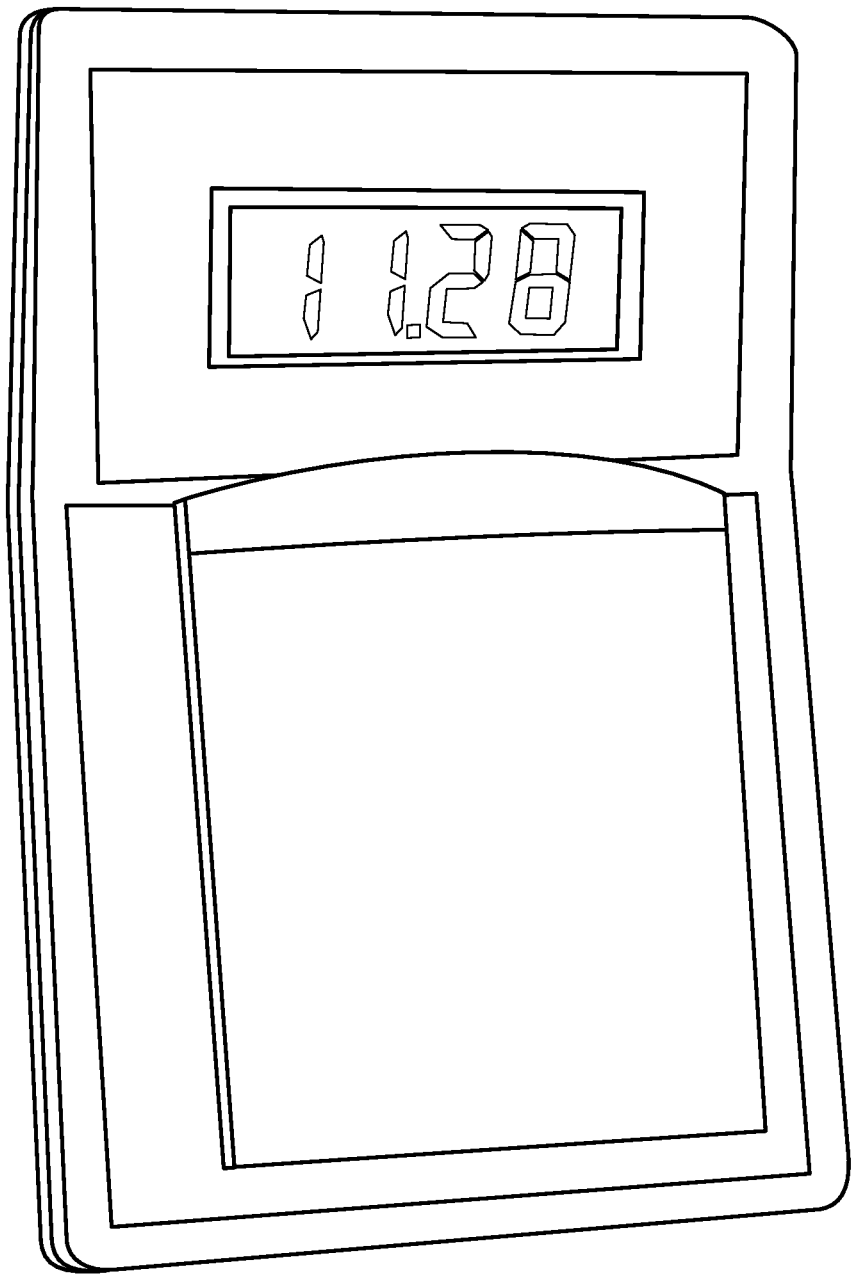
FIG. 1a shows one example of the data gathering device of the invention, a portable digital data gatherer with numerical LCD readout.

The present invention is an article of manufacture and method for using same. Comprising at least two sensors having an offset potential of below about +/−1.0 mV; and a data-gathering device connected to the sensors capable of measuring the voltage differential between the sensors. The sensors preferably are AgCl coated Silver.

It is a key feature of the preferred embodiment that low offset potential sensors are utilized in the present invention. As mentioned above, low offset potential sensors allow (the low artifact) detection of the very (small voltages) generated as a result of SNS and PNS changes in tone. Sensors of the prior art had higher offset potentials which act as noise artifact and confound the measurement of the small, desired signal voltages. The offset potential difference between the sensor pair of the sensors of the present invention should be below about +/−1.0 mV, and are preferably below +/−0.5 mV, and most preferably about +/−0.01 mV. Preferred sensors are model GS-26 from Bio-Medical Corp. (Warren, Mich.), although any sensors meeting the criteria stated herein will be sufficient for the purposes of the invention.

In addition, the sensors of the present invention should have a coating sufficient to conduct the small voltages due to SNS & PNS activations but should not create offset potentials of similar magnitudes. As previously mentioned, aluminum sensors or other crystal lattices can create a higher offset potential. The most preferred coating for the sensor is an AgCl coating. The coating can deposited electrolytically deposited and be of any thickness, although coatings of higher thicknesses are more durable and less prone to scratching. Other materials or coatings may be suitable, such as gold, so long as they achieve the offset potential requirements of the present invention. The AgCl compound is most preferred.

It is also preferable that the sensors be coated with a conductive gel. The conductive gel is preferably applied by a mechanical process that allows for the gel to be applied in a consistent manner, and with a minimum of air bubbles. In most cases, this will mean that the gel is pre-applied utilizing a mechanical process at a factory. However, as used herein, the term pre-applied can refer to any process that allows for a consistent application of the conductive gel, i.e., a gel that is applied with a consistent thickness across the sensor and in a manner so that conductivity is consistent from electrode to electrode. This may mean that the gel is applied in a manner which creates a minimum of air bubbles or at least a consistent amount of air bubbles from sensor to sensor.

The sensors of the present invention will also most likely have a means for adhering the sensors to the subject. Any method of adhering the sensors to the subject is acceptable, as long as it does not interfere with the ability of the sensor to acquire the sensor to sensor voltage. For example, the electrodes could be taped to the subject. In a preferred embodiment, the sensor has a collar around the outer diameter of the electrode, which has an adhesive applied thereto. The sensors can be affixed anywhere on the subject, as long as they are affixed contralaterally in an identical manner. Preferably, the electrodes are affixed in identical positions on either side of the body, for example, on the palms of a humans' hands or opposite sides of their neck.

The size of the electrode depends on the type subject, and on which body part the sensor is to be attached. The device of the present invention can be used for either humans or animals. For humans, a sensor of 50 mm or less is desirable, and if the sensor is to be attached to the palm of the hand, a sensor of 10 mm is most desirable. For large animals such as horses, sensors of up to 50 mm or larger may be appropriate. Therefore, it is anticipated that the size of the sensor will be selected appropriately for the type of subject as well as the expected place of placement thereon.

The data gathering device of the present invention can be any device suitable for detecting the signals generated during the measurements. For example, the device can be an analog meter with a digital readout that simply reports the voltage differentials between the electrodes. An illustrative example is seen in FIG. 1a. Or, in the alternative, the data gathering device can be a stripchart recorder typically used to monitor EKG outputs. The data gathering device can also have a memory which allows it to record the data of one or more subjects over a period of time. The data gathering device can potentially be linked with a computer having software to maintain and analyze subject data. It can also consist of an analog dial to display the strength of the reading.

Figure 2:
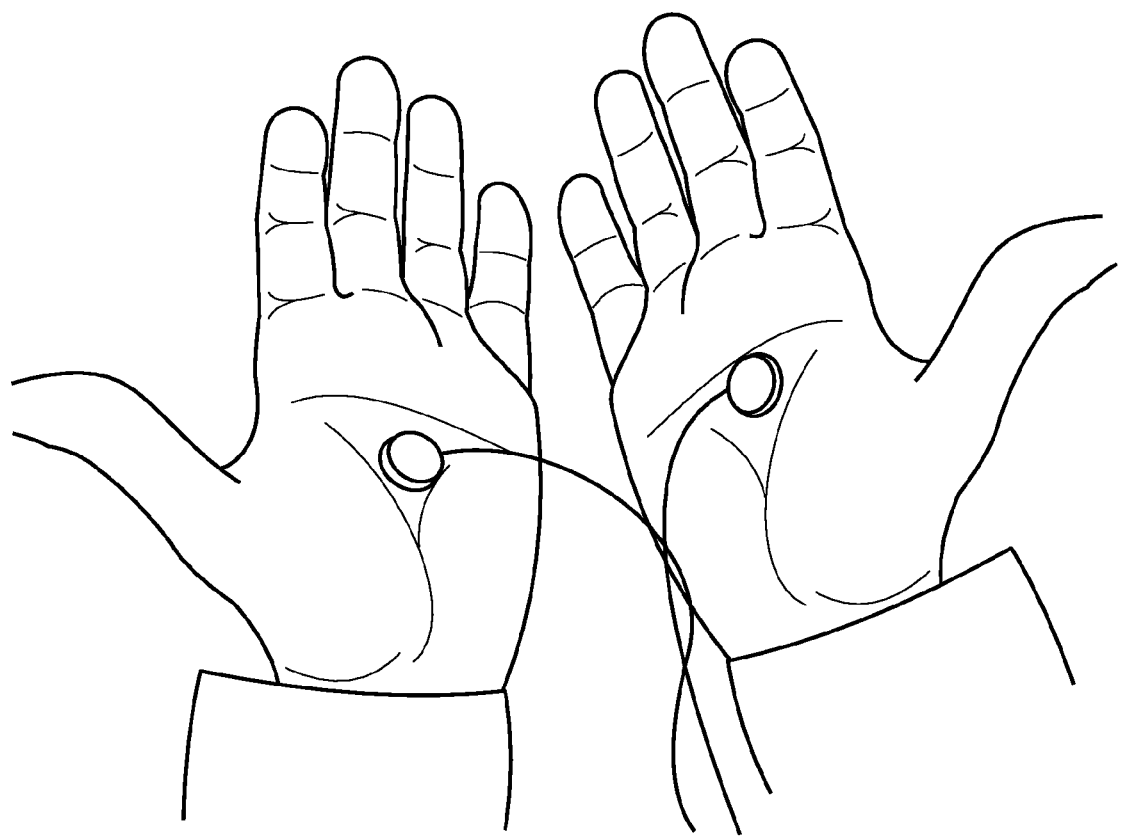
FIG. 2 shows an example of use with humans wherein the electrodes are applied to the center of the subject's palms.

In preferred embodiments of the present invention, the examiner uses disposable, low-offset-potential biomedical sensors (offset of less than 0.5 millivolts) with adhesive collars, a covering of conductive gel applied at the factory, and an actual diameter of the sensor of approximately 10 mm, designed for use with humans. Each subject should be allowed to rest quietly for ten minutes before the measurement process begins. Preferably, the subject refrains from coffee or other stimulants for three hours before the measurement session. The present invention begins with the placement of the self-adhesive, extremely low-offset-potential electrodes. On humans this may be advantageously achieved by placing one sensor in the center of each palm. The same site on the palm should be used on each hand. See FIG. 2. However, other sites on the body can be used so long as care is taken to select identical sites on both left and right sides of the body. An alcohol swipe of the sites to remove excess skin oils (which can inhibit conductivity) may be performed prior to electrode placement. During the measurement process, the subject should be asked to remain still and relax.

Figure 1B:
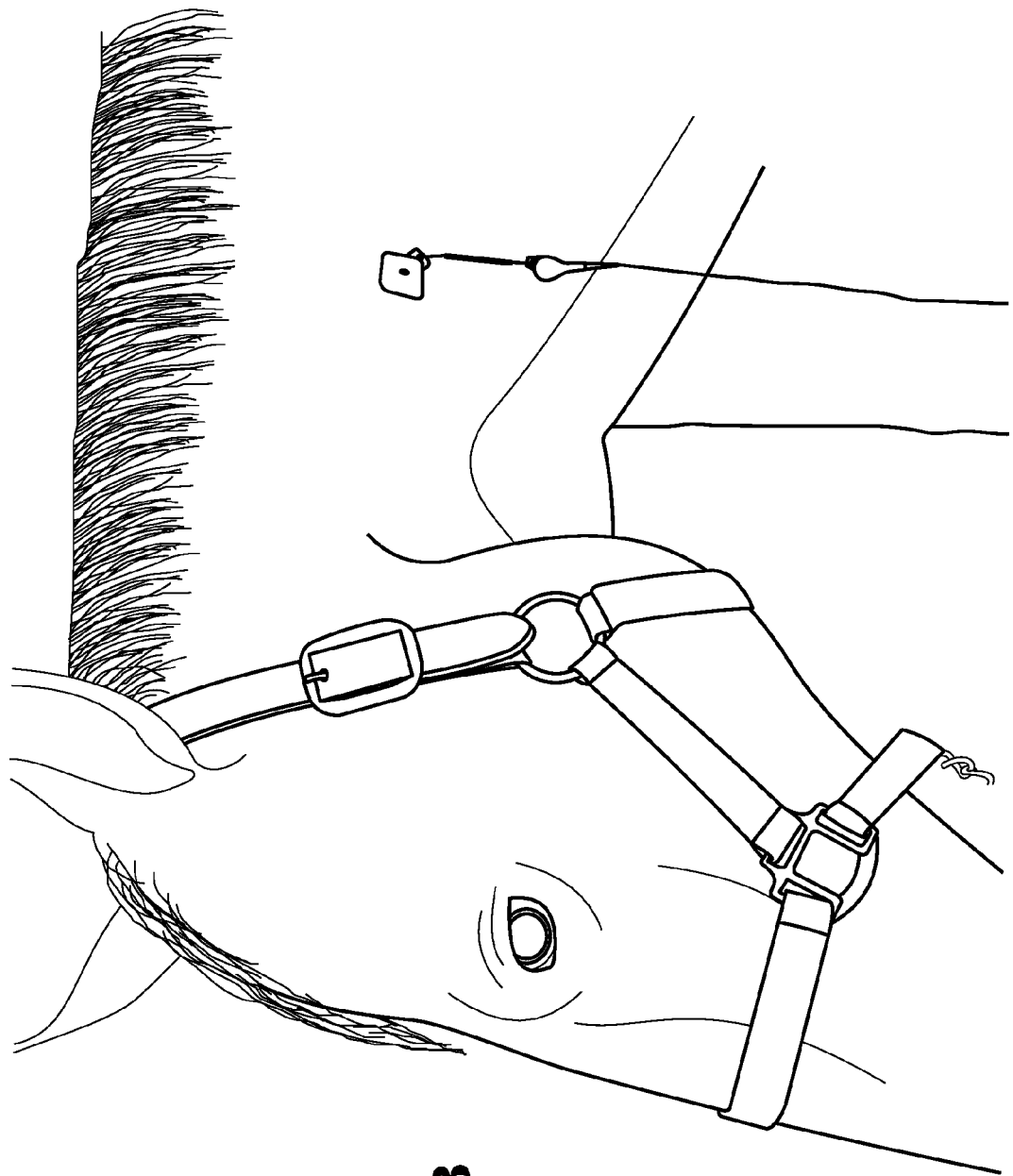
FIG. 1b shows an example of the present invention for use with animals, wherein the electrodes are applied to identical spots on contralateral sides of a horse's neck.

Abrasion of the skin can also be used to obtain still better conductivity. To insure identical conditions, each palm is preferably treated the same way to (e.g., use an identical number of strokes of the alcohol pad or abrasive on each palm, and use a different side of the pad for each palm). On short haired animals such as horses this can be achieved by using other contralateral electrode sites, such as both sides of the neck, (see FIG. 1b) which may require shaving of the electrode site and preparation with an alcohol swipe. Alternatively, a conductive gel may be used to obtain valid readings through a coat of hair or fur if it is not too thick.

During readings on humans, the subjects preferably sit upright, with the backs of their hands resting on the top of their thighs. Care should be taken to avoid pressure on the wires or the electrodes. Subjects should then be asked to remain still, close their eyes, and relax for the duration of the reading. If a non-digital data gatherer is used, such as a strip chart recorder, an ear clip ground should be employed. This is in the form of a silver clip attached to the right ear lobe, with a lead wire that plugs into the ground input receptacle of the recorder. This ground wire substantially limits electrical interference by other people moving nearby in a busy clinical environment. For animal subjects and non-verbal humans, the subject should be kept as stationary as possible.

In interpreting results, care should be taken to spot ANS disruptions caused by impatience or anger on the part of the subject from frustration or annoyance of being perhaps restrained for the measurement. It should be noted that a minority patients, when measured in the afternoon after lunch, have negative readings when in a pain free state. Patient readings should be double checked or measurements done in the morning if this phenomenon occurs for a particular patient.

To avoid the above problems with restraint, a hand-held measuring unit with battery-powered data logger can be moved alongside the individual while they move about. Similarly, subjects with conditions that only manifest pain during movement (for example, walking or bending) can be tracked while they move. Decreases in the values of readings during movement can be taken to indicate pain that is induced by the movement.

After preparation of the sensor site with alcohol pads, special self-adhesive sensors with low offset potential are then peeled off their sheet and pressed onto the skin at the proper site. The individuals performing the measurement should run their thumb firmly around the top surface of the electrode's adhesive collar and press down on the metal electrode snap itself to assure that both electrodes are firmly affixed. It is preferred that the entire gel coated metal sensing surface be in contact with the skin on both sites on the subject. It is also preferred to treat each electrode the same way in order to achieve identical conditions on both contralateral sides. If, after removal of the electrodes, the examiner wishes to take another measurement, the alcohol swipe should be repeated to remove any adhesive residue on the skin from the first measurement.

Next the lead wires are attached to the electrodes by clips or snaps. The lead wires are connected across a load resistor of from 0.5 k to 500 k Ohms, preferably 22 k Ohms, at a data gathering device such as a chart recorder, digital data logger, or other device. The voltage difference between the lead wires in series with the voltage's source resistance (representing the "resistance-containing" voltage source between the left and right sides of the body) produces a voltage drop across the load resistor which then "feeds" the data gathering device. The data gathering device can produce both numerical values and/or a continuous line on a volts vs time graph, either or both of which constitute the reading. The Y-axis displays the resistance-divider modified voltage of the incoming signal. Increases in voltage or decreases in voltage-source-resistance between the left and right sides of the body, will increase the Y value. Sometimes the subject's reading or "trace" will be a fairly horizontal line on the graph. Often it will start out high above the Y=0 "baseline" (i.e. positive numerical values) and then, as the subject relaxes, begin to move downwards towards the Y=0 baseline. Under normal circumstances, a trace will occur directly on the Y=0 baseline if the voltage between the sensors is 0. Usually by the one minute mark the trace will have stabilized at a "plateau" and remain relatively steady. If this has not occurred, the measurer may wish to continue the trace for another minute.

After 60-120 seconds, the recorder can be switched off. The reading may now be interpreted. While useful information may be obtained from the entire trace, the degree to which the trace may be above or below baseline at the end of the trace should be observed. The record of the trace may be stored in a paper file or in a computer. The entire process, from site prep to storing the recording takes approximately 3-5 minutes and can be performed by a minimally trained individual. Presence or absence of moderate to severe pain can usually be confirmed with a glance at the graph to see whether the subject's trace is above or below Y=0. If it is below Y=0 (i.e. negative numerical values), the subject can be assumed to be in moderate to severe pain, unless other confounding factors are at work (ANS dysfunction, etc.) If the trace is above Y=0, the subject can be assumed to be pain free or experiencing pain below a level of 4 on the 0-10 Visual Analogue Scale (VAS), as has been determined by large numbers of measurements that have been taken on subjects reporting their pain state on the 0-10 VAS at the time of measurement.

This same protocol should be used even when the measurement is being taken for purposes other than the confirmation of the presence or absence of significant pain (e.g., searching for disruptions in ANS balance produced by other causes).

Lead wires from the electrodes should be connected to the data gatherer in a pre-determined manner such that lower voltage on the right hand (vs. the left) will produce a trace below the zero baseline, or Y=0 and give negative numerical values.

If analysis of more rapidly changing signals is desired, a data gatherer with sampling rates faster than 1 per second should be used along with a commensurate increased bandwidth "anti-alias" filter. A trace should then be taken while the subject engages in controlled breathing or Valsalva maneuver or other known vagal triggers for a minimum of one minute. The data gatherer will record SNS tone increases in response to inspiration (breathing in) and PNS tone increases in response to exhalation. On a graphic display, the difference between the high peaks and the low valleys provide the lability of that individual's ANS. In a graphic display, or trace, of a subject's recordings taken during normal breathing for diagnostic purposes, the distance of traces below the zero baseline can then be expressed in terms of percentage of total ANS lability. If the display being used is numerical, adding the absolute values of the greatest positive voltage readings to the absolute values of the greatest negative voltage readings will equal the maximum ANS lability of the individual (e.g., positive 2.0 mV+negative 1.5 mV=3.5 mV total lability). This can allow the investigator to, for example in the case of pain, estimate how significant the negative displacement of the trace below Y=0 is for that given individual. This can be used to account for a decrease in the degree of ANS lability associated with age, and/or the fact that some individuals simply have more ANS lability (for example, are more excitable) than others. Therefore this controlled breathing measurement procedure allows a quantitative estimate of the subject's condition to be made without obtaining a prior baseline. The baseline reading can be obtained during controlled breathing when the subject comes in for the first visit to obtain treatment or investigation of their condition. Similar analyses can be performed using other known clinical vagal triggers such as the Valsalva maneuver.

When tracking of rapidly changing signals is not required, a lower rate of sampling (once every second to once every few seconds) along with a narrower bandwidth anti-alias filter will provide a smoother, more easily interpreted trace, one that eliminates much of the moment-to-moment swings caused by respiration. When faster tracking is desired, the examiner may advantageously first measure with the fast sampling rate and broader filter during controlled breathing and save this record. Next he or she may measure with the slower sampling rate and narrower filter and take the reading at the 60 second mark to allow calculation of the sixty second reading as a percentage of total lability. This observed value can then be compared to established databases, thus indicating a range of pain levels associated with a given degree of deflection from the neutral, zero baseline for that given individual being measured.

Paper records from a chart recorder can be torn off and stored in the patient's folder. With computer-linked digital data recorders, both the numerical readings and the graph can be printed on paper and inserted in the patient's chart and/or stored electronically as a file in the computer. Furthermore, such electronic files can be analyzed by sophisticated statistical analysis programs, and such files can be e-mailed to a colleague for consultation if the colleague has the same software installed on his or her computer.

If grossly unexpected results are obtained, there may be one of two problems present. One of the sensors may have adhered to the subject loosely. If this is suspected, simply repeat the measurement to confirm. However, if connections seem to be of equal quality on both sides, then the examiner should remove the sensors and check their offset potential. Even specially manufactured low-off set-potential sensors can sometimes have a defective unit in a batch. Carefully peel off the sensors from the subject and place them together so that the exposed gelled metal sensing surfaces (i.e. the gelled surface contacting the skin) of the two sensors are precisely atop one another. Press them and their adhesive collars firmly together so that the adhesive collars keep the gelled surfaces in contact. Connect lead wires to the sensors and take a reading. Readings obtained should be on the order of less than 0.2 mV. If readings substantially above this are obtained, then the offset potential may be grossly affecting the subject's reading magnitude and the entire measurement process should be repeated.

Problems of high offset potential may be due to the nature of the sensors or the chemical compound coating the sensors. Pure metals generally form sizeable half-cell potentials. That is, interaction between the salt water of the subject's perspiration (always present on the skin to some extent) reacts with the metal to generate a half-cell voltage. This artifact can overwhelm the small signals being acquired in the two-sensor-site measure of the present invention. At a minimum, it will affect the numeric reading of the site to site voltage. AgCl coated Ag electrodes of the type employed in the present invention were developed precisely to counter this effect. These are pure standard metals, such as silver, but the area in contact with the skin contacting gel is coated with an electrolytically formed silver-chloride layer. These have much lower offset potentials than most other sensors. However the thin coats of AgCl are easily scratched and therefore it is preferred to use disposable Ag/AgCl sensors in order to insure consistency of readings.

However, even Ag/AgCl sensors may have offset potentials on the order of several millivolts. This is measured by pressing two sensors together and measuring the effect. The site to site voltage difference measured without skin abrasion in the present invention is often less than a millivolt. Thus offset potentials can overshadow this signal and produce erroneous results. Clearly, the use of low offset potential electrodes allows meaningful data to be obtained during the type of measurements that constitute the method described here.

There are numerous uses for the present invention including measuring the effects of various agents on SNS and PSNS tone, including but not limited to: beta blockers, atropine, scopolamine, beta-adrenergic blockade, sedatives, anti-anxiety medications, analgesics, anesthetics, narcotics, and others. Thus the proposed method may help in titration of medicines and/or determining the effectiveness of a particular medication for a given subject. The method may also help in diagnosing conditions that involve altered ANS function, including but not limited to: certain types of hypertension, Parkinson's disease, multiple sclerosis, Guillain-Barre syndrome, and orthostatic hypertension of the Shy-Drager type. In some of these disorders, changes in PNS tone may be useful in quantitating the rate of disease progression and/or the effect of therapeutic intervention. Identifying changes in PNS tone may help in identifying fetal and neonatal distress and identifying those at high risk of sudden infant death syndrome.

EXAMPLES

For the examples described below the following procedure was followed: Unless otherwise noted, the examiner used disposable, low-offset-potential biomedical sensors model GS-26 from Bio-Medical Corp. (Warren, Mich.), with adhesive collars, having a covering of conductive gel applied at the factory. When humans were measured, the subject was allowed to rest quietly for ten minutes before the measurement process started. A self-adhesive, extremely low-offset-potential sensor was placed in the center of each palm. An alcohol swipe of each palm to remove excess skin oils (which can inhibit conductivity) was performed prior to sensor placement and an ear clip ground was employed if other individuals were moving around a Chart Recorder based data gathering setup. The subject was asked to remain still and sit upright, with the backs of their hands resting on the top of their thighs, and to sit in a relaxed position with their arms limp. When horses were measured, the horse's neck was shaved and the sensors placed on both sides of the neck, (see FIG. 1b).

The lead wires were connected at their opposite ends to a data gathering device. In the case of the data generated for FIGS. 4 to 7, the data gathering device was a recorder available from Kipp & Zonen, Model BD112, (Delft, Holland). For data generated for FIGS. 3, and 8-13, the recorder was a Biographs, LLC, PT-05 PainTree™. The device was switched on, and data recorded for a period of 2-3 minutes. The machine was turned off, the electrodes removed from the subject, and data interpreted.

Example 1

Figure 3A:
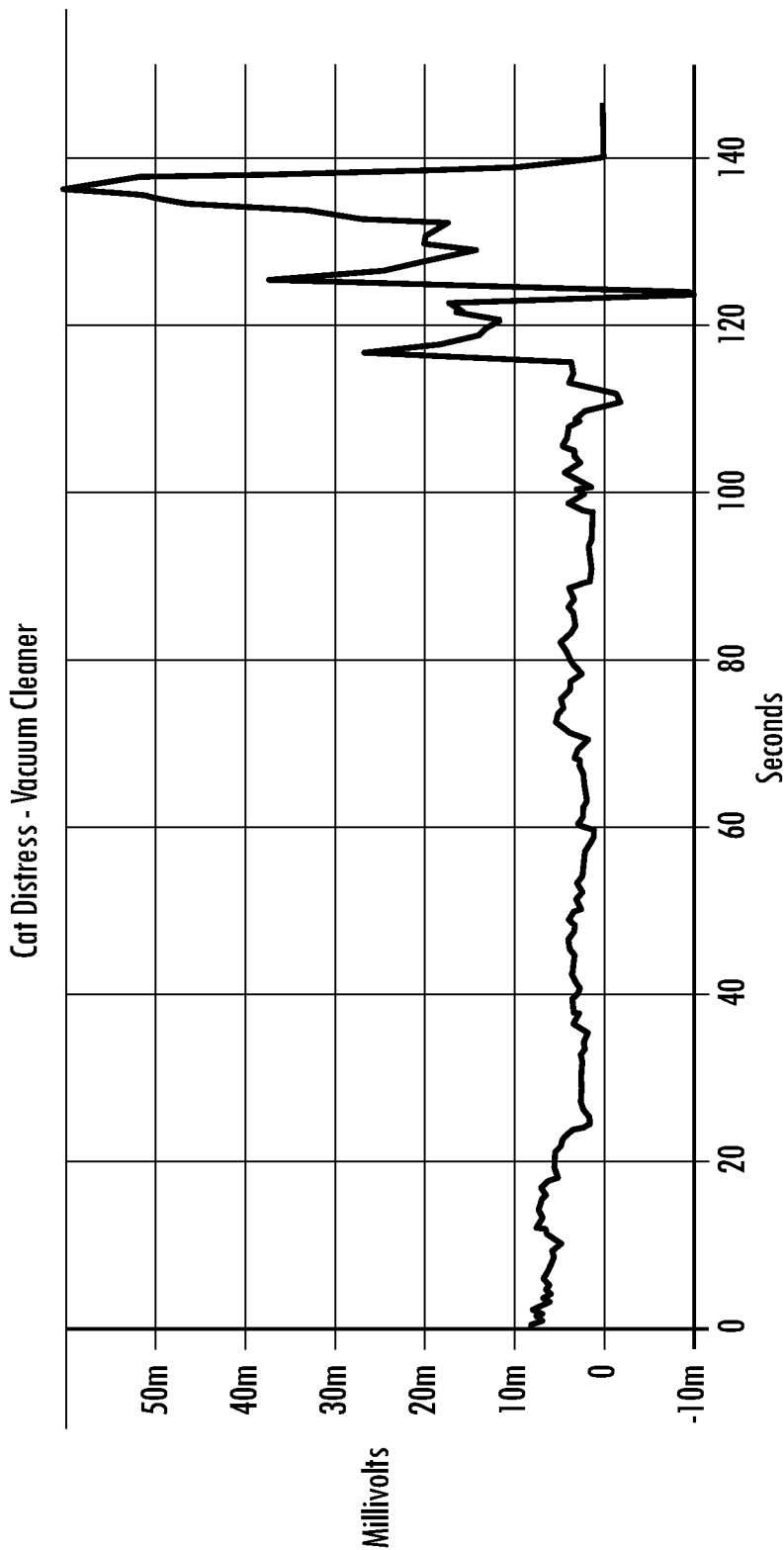
FIGS. 3a and b show examples of graphic display of a pain reading of an animal, on a computer, showing the effects of a known ANS trigger, namely, the effect of a vacuum cleaner noise in proximity to a cat.

FIGS. 3a and b show examples of the graphic display of a reading on a computer, showing effects of a known ANS trigger. Specifically, FIG. 3a shows distress in a cat. The sensors were placed on the cat's paws. The computerized trace shows a rise in sympathetic tone (upward movement on the Y-axis) known to be associated with distress in animals caused by proximity of an operating vacuum cleaner. Vacuum was switched on at 107 seconds (X-axis) and moved closer until at 140 seconds after measurement began, the cat fled the device.

Figure 3B:
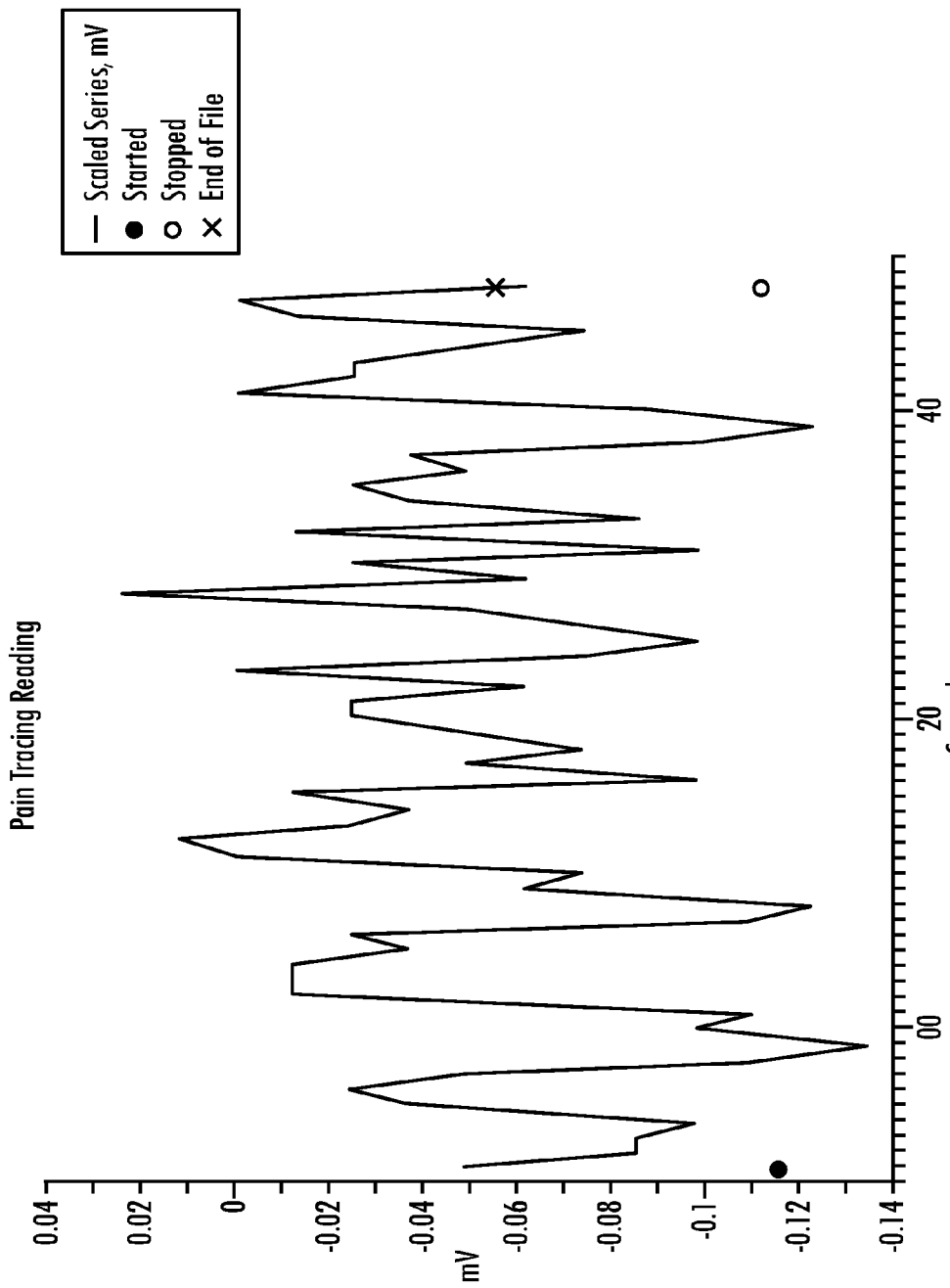

FIG. 3b shows a human doing controlled breathing: Trace rising and falling (re. Y-axis) illustrates the known ANS effects of controlled breathing. Inhalation causes a rise in sympathetic tone (rise in trace on graph) and exhalation causes a rise in parasympathetic (i.e. vagal) tone (fall in trace). This 41 year old female human was inhaling for 5 seconds (x-axis), followed by exhaling for 5 seconds, for approximately one minute. This type of controlled breathing is a classic medical technique used in the study of ANS function.

Example 2

Figure 4:
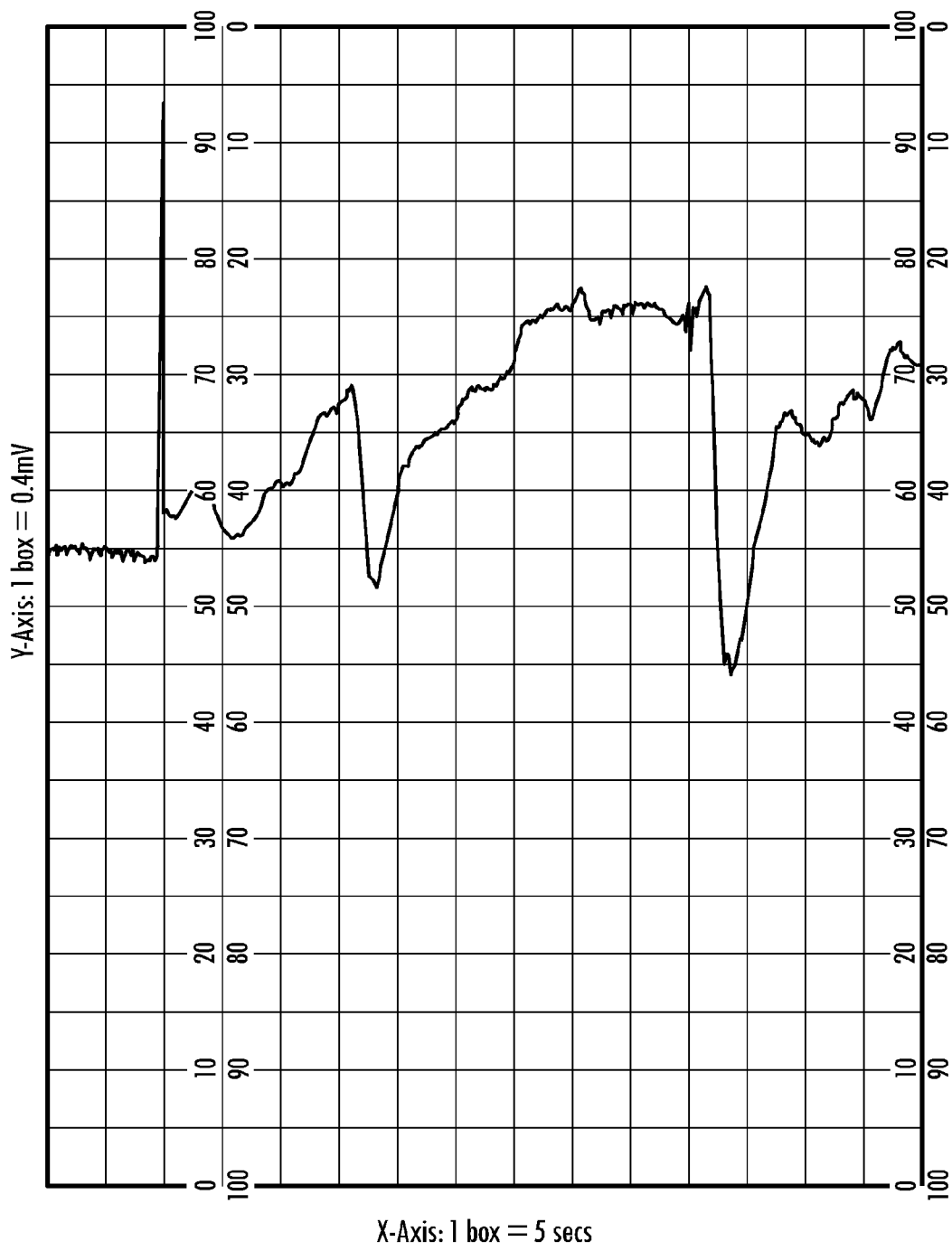
FIG. 4 shows epilepsy-like alterations in ANS activity.

FIG. 4 shows epilepsy-like alterations in ANS activity: Reading depicted on strip chart recorder is for a 75 year old male with sporadic, pronounced, and uncontrollable hand tremors. As is known to happen with some types of epilepsy, the seizure-like activity occurs at the peak of a rise in sympathetic tone (rise of trace on Y-axis) and is immediately followed by a strong rise in parasympathetic tone (shown by a fall in subject's trace on the Y-axis) as the body attempts to restore homeostasis. This example depicts how the proposed method may help diagnose non-manifesting forms of epilepsy, as well as catch epileptic-like activity early in its development with a subject before it grows into full-blown seizures Likewise, such measurements might help the physician titrate the dosage of seizure medications.

Example 3

Figure 5A:
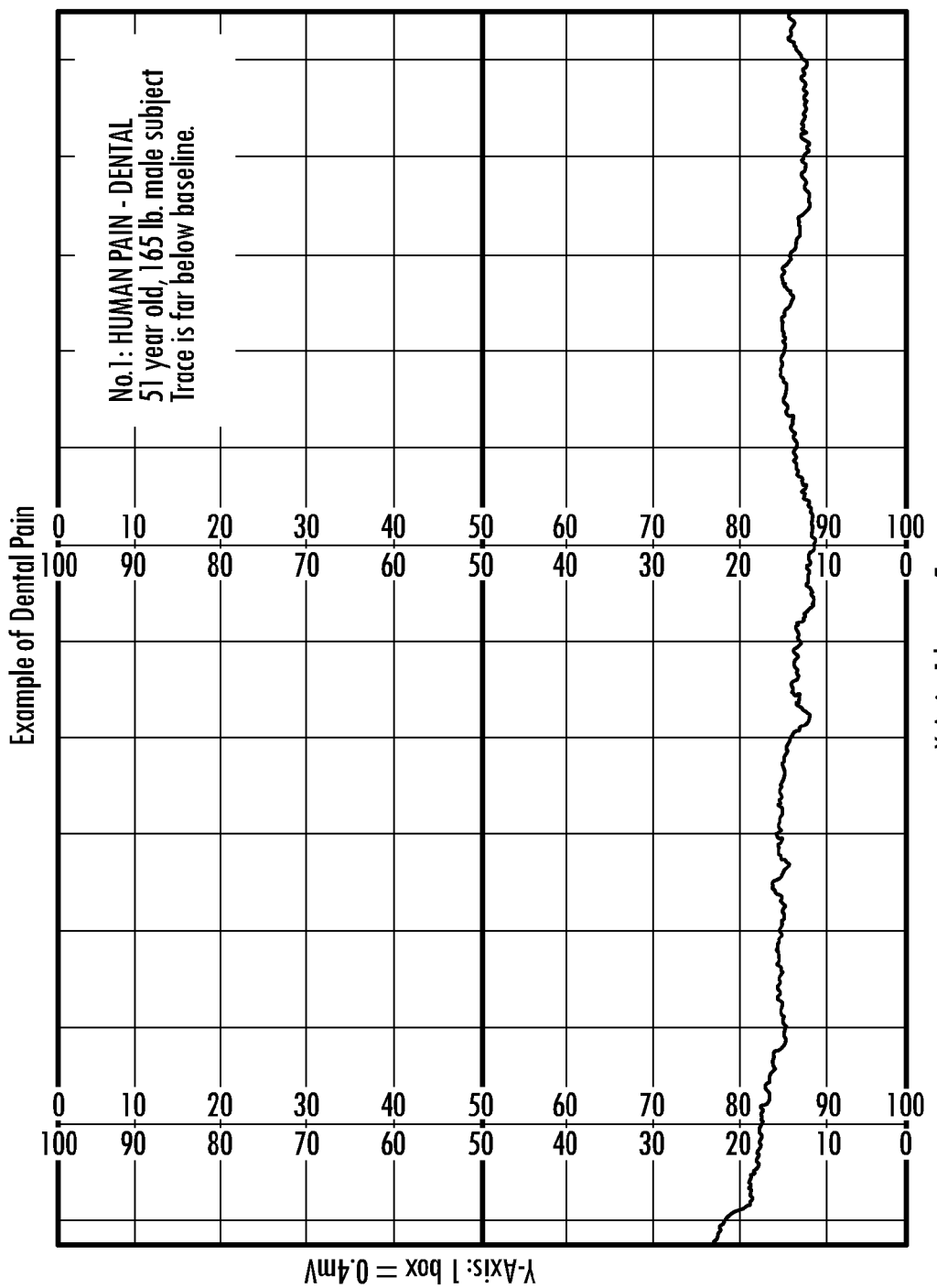
FIGS. 5a-d show dental pain and pain relief in a 51 year old male human, depicted on a strip chart recorder.
Figure 5B:
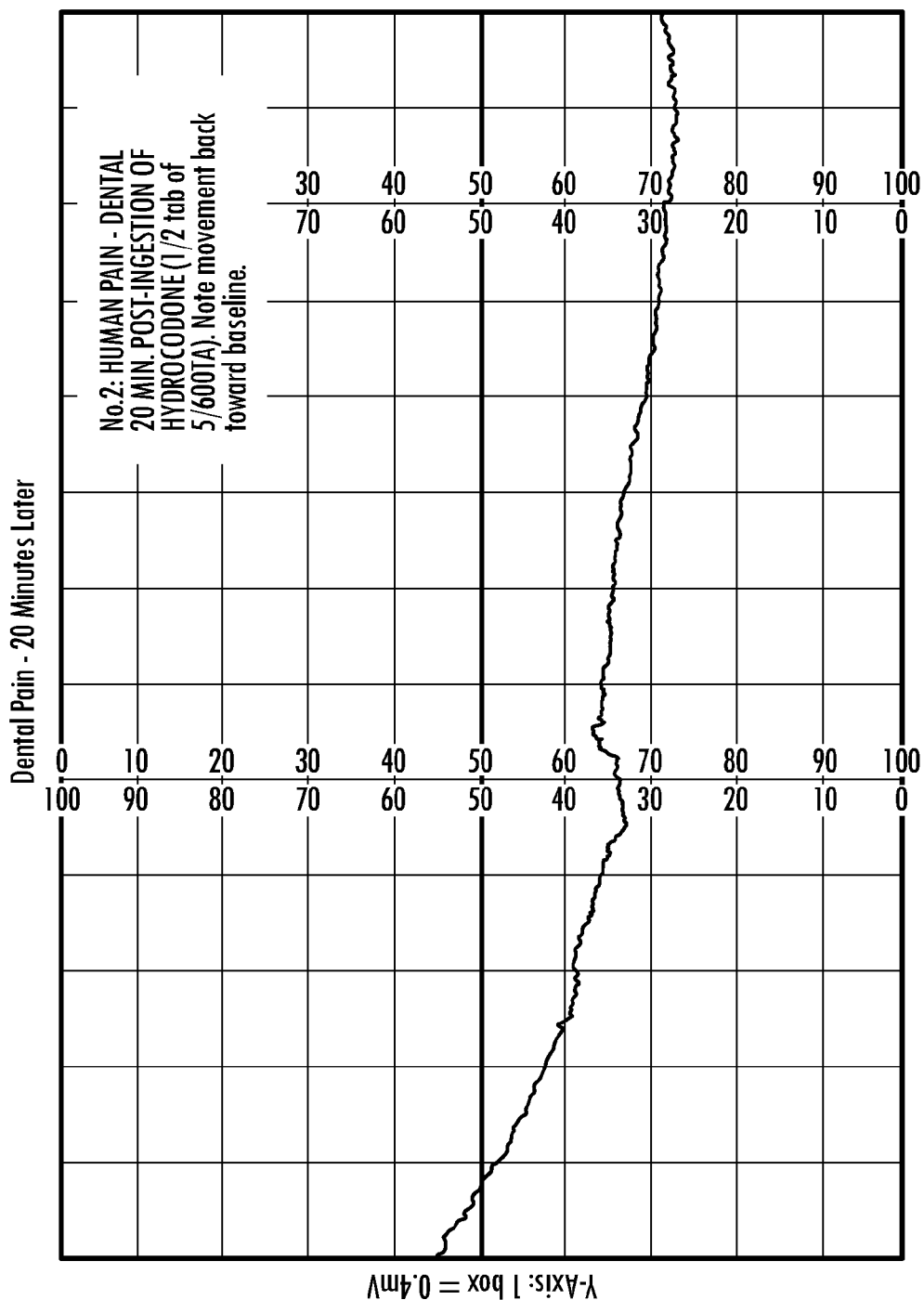
Figure 5C:
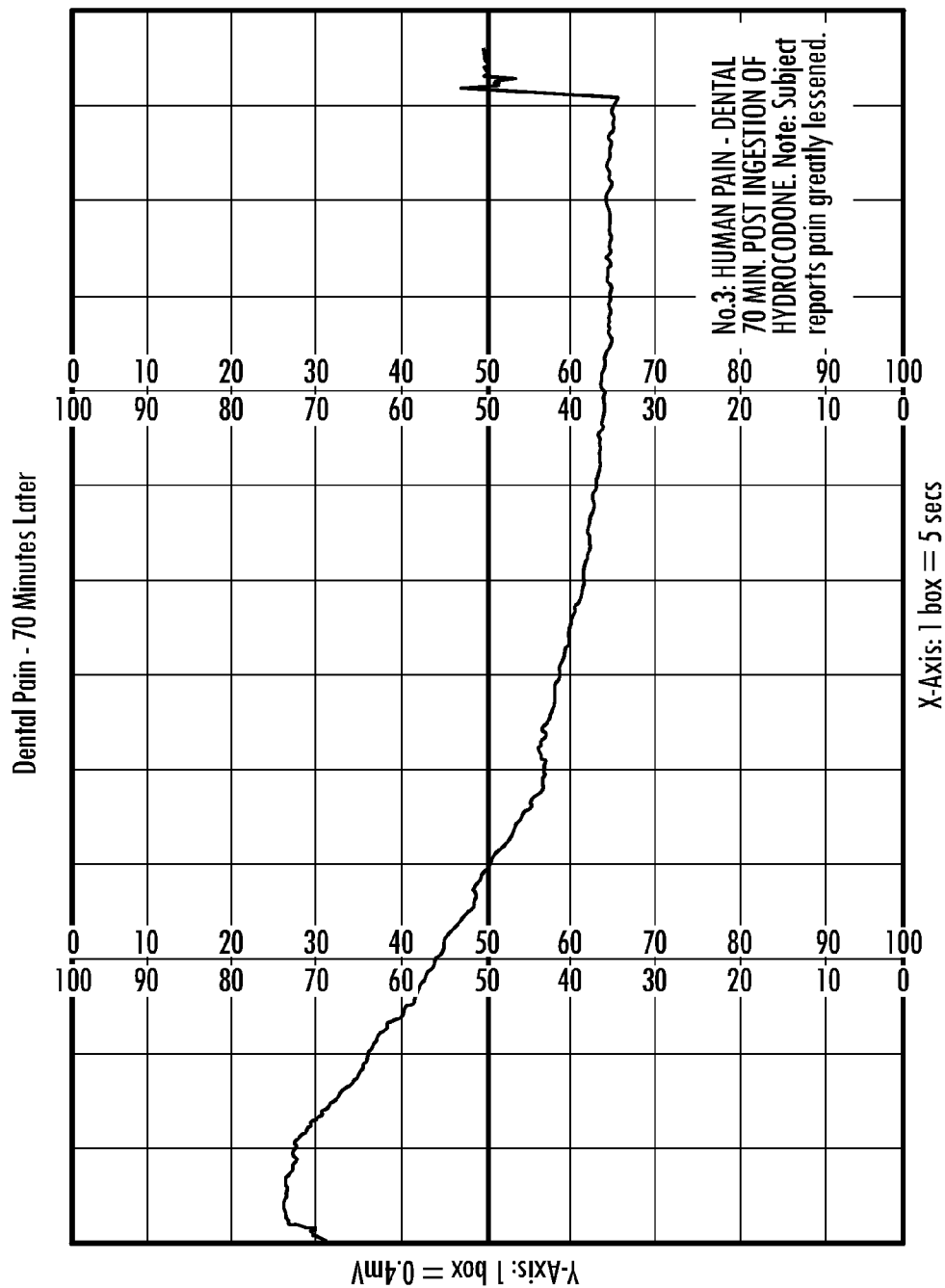
Figure 5D:
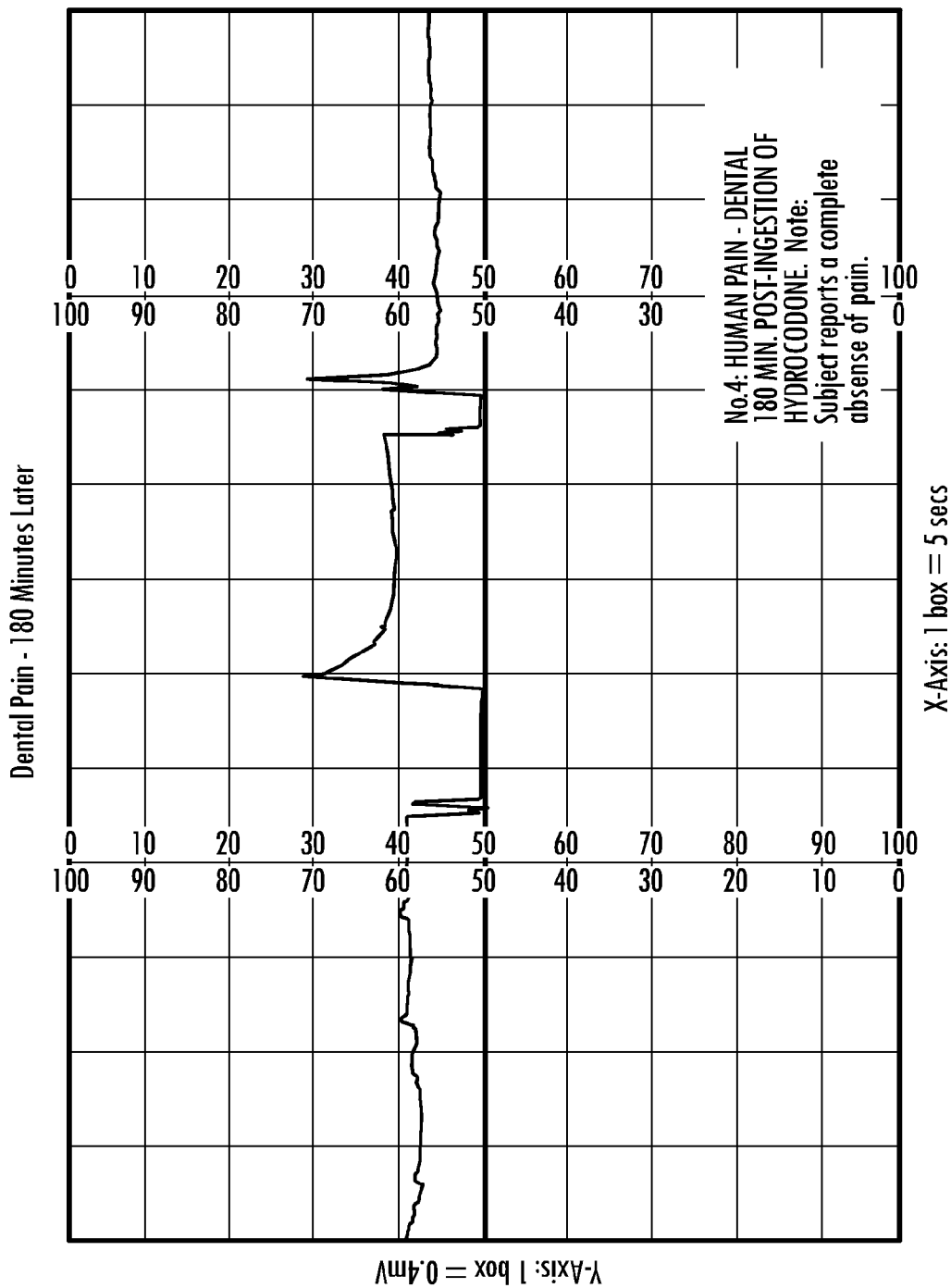

FIGS. 5a-d show dental pain in 51 year old male human, depicted on strip chart recorder. In FIG. 5a, the subject reports substantial pain. Trace is well below the X axis, indicating moderate to severe pain. In FIG. 5b, the same subject is shown 20 minutes after ingestion of oxycodone (½ tablet of 5/500TA). Trace is rising slightly. In FIG. 5c, 70 minutes after oxycodone ingestion, half of trace is above X-axis. Subject reports significant pain relief. In FIG. 5d, 180 minutes after oxycodone ingestion, subject is pain free and trace is completely above X-axis in 3 separate measurements. Oxycodone is known to take 3 hours to achieve its full effect.

Example 4

Figure 6A:
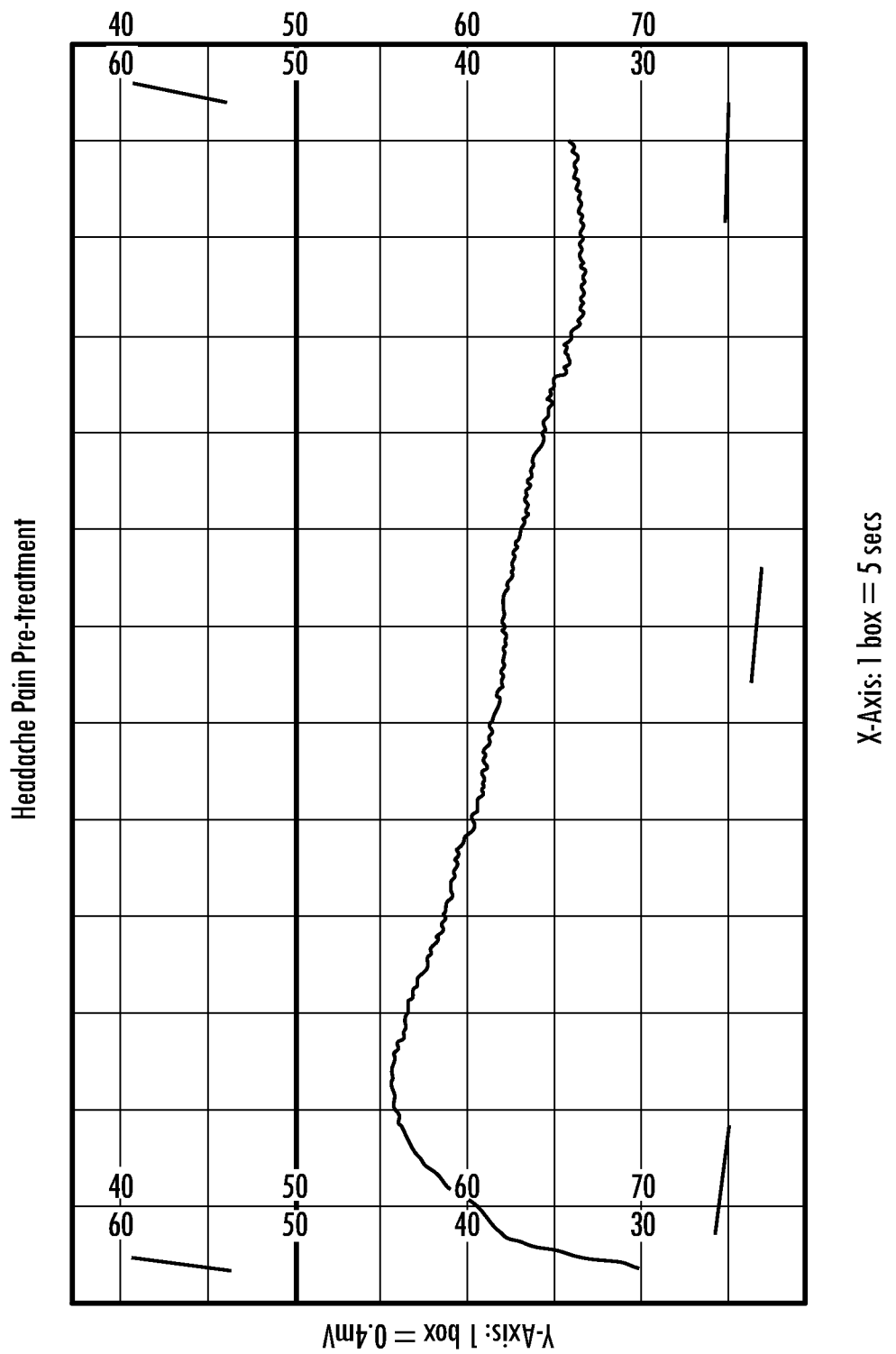
FIGS. 6a-c show headache pain and pain relief in humans, depicted on strip chart recorder.
Figure 6C:
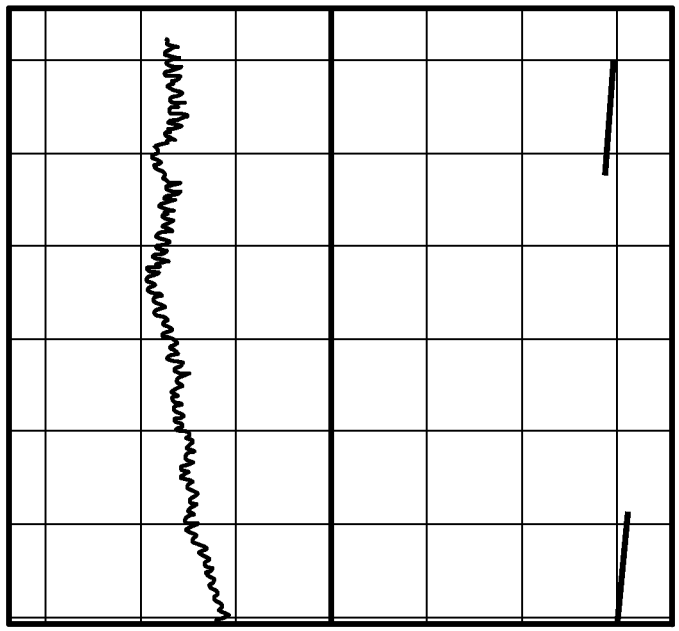
Figure 6B:
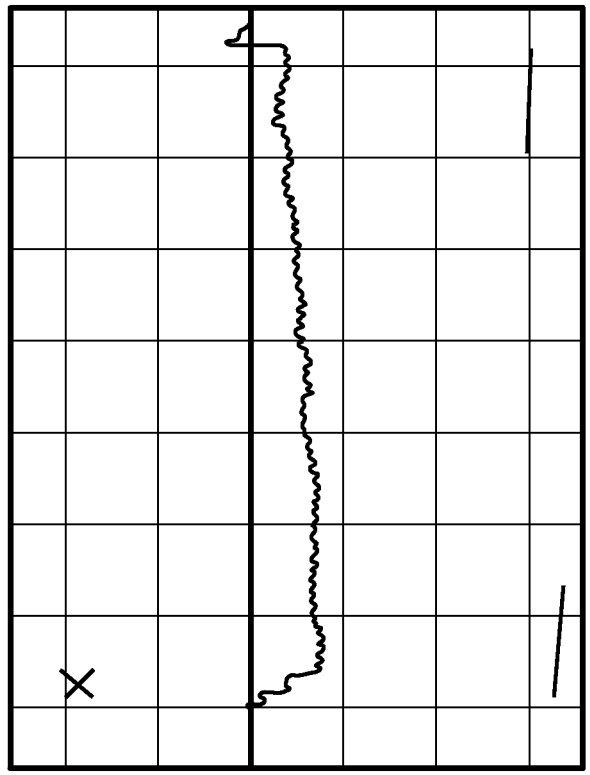

FIGS. 6a-c show headache pain in humans, depicted on strip chart recorder using methods disclosed in U.S. Pat. No. 6,347,238. In FIG. 6a, a 35 year old female reports severe headache pain. Trace of reading is well below X-axis, indicating moderate to severe pain. FIG. 6b shows the same subject one hour after ingestion of Excedrin Migraine®. medication. Subject reports that pain has greatly lessened. Trace is almost back to X-axis. 135 minutes after ingestion of medication, FIG. 6c shows the subject is pain free and the trace is now well above X axis, indicating a pain-free state, which agrees with the subjects self-report.

Example 5

Figure 7A:
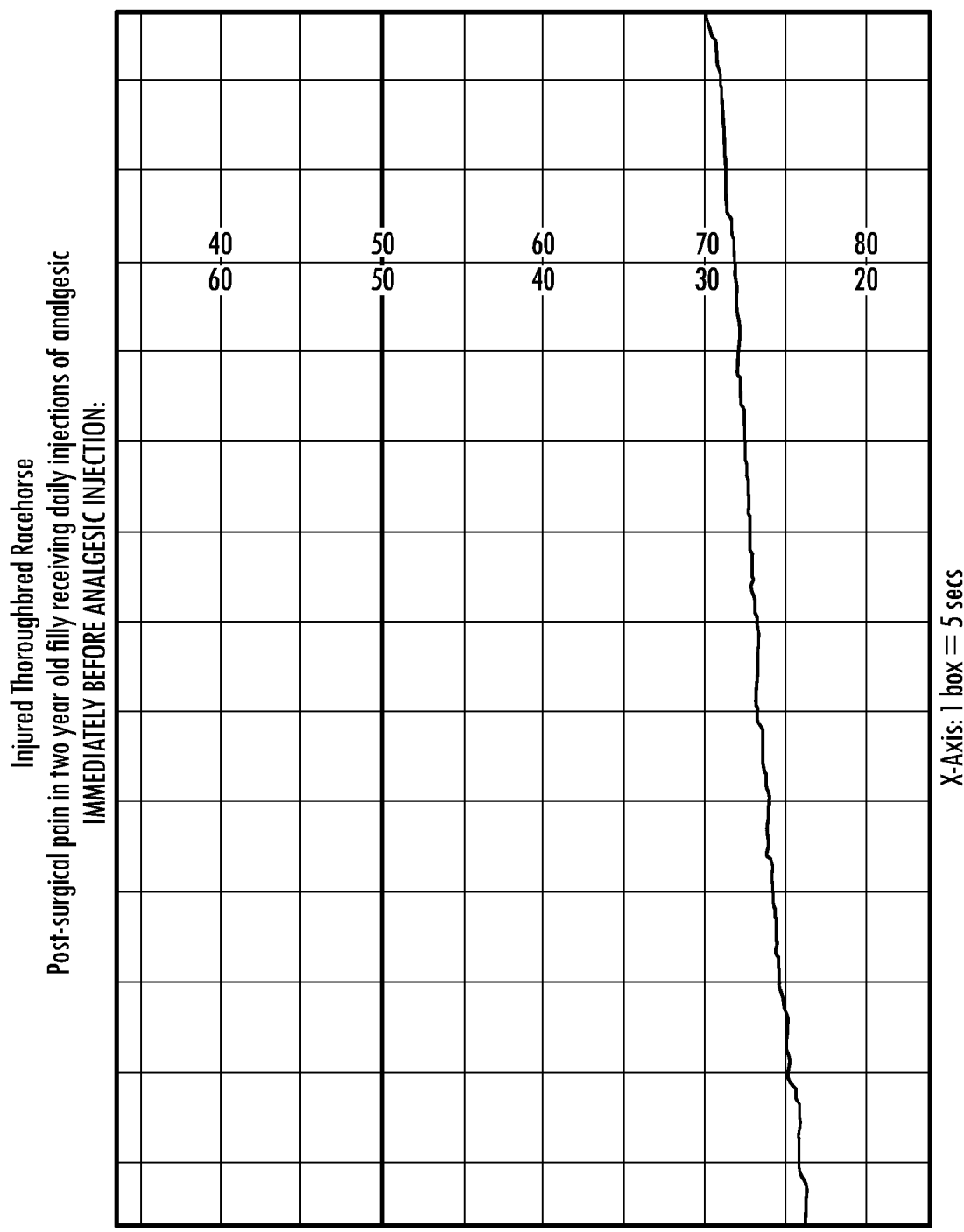
FIGS. 7a and b show pain and pain relief for horses, as shown on a strip chart recorder.
Figure 7B:
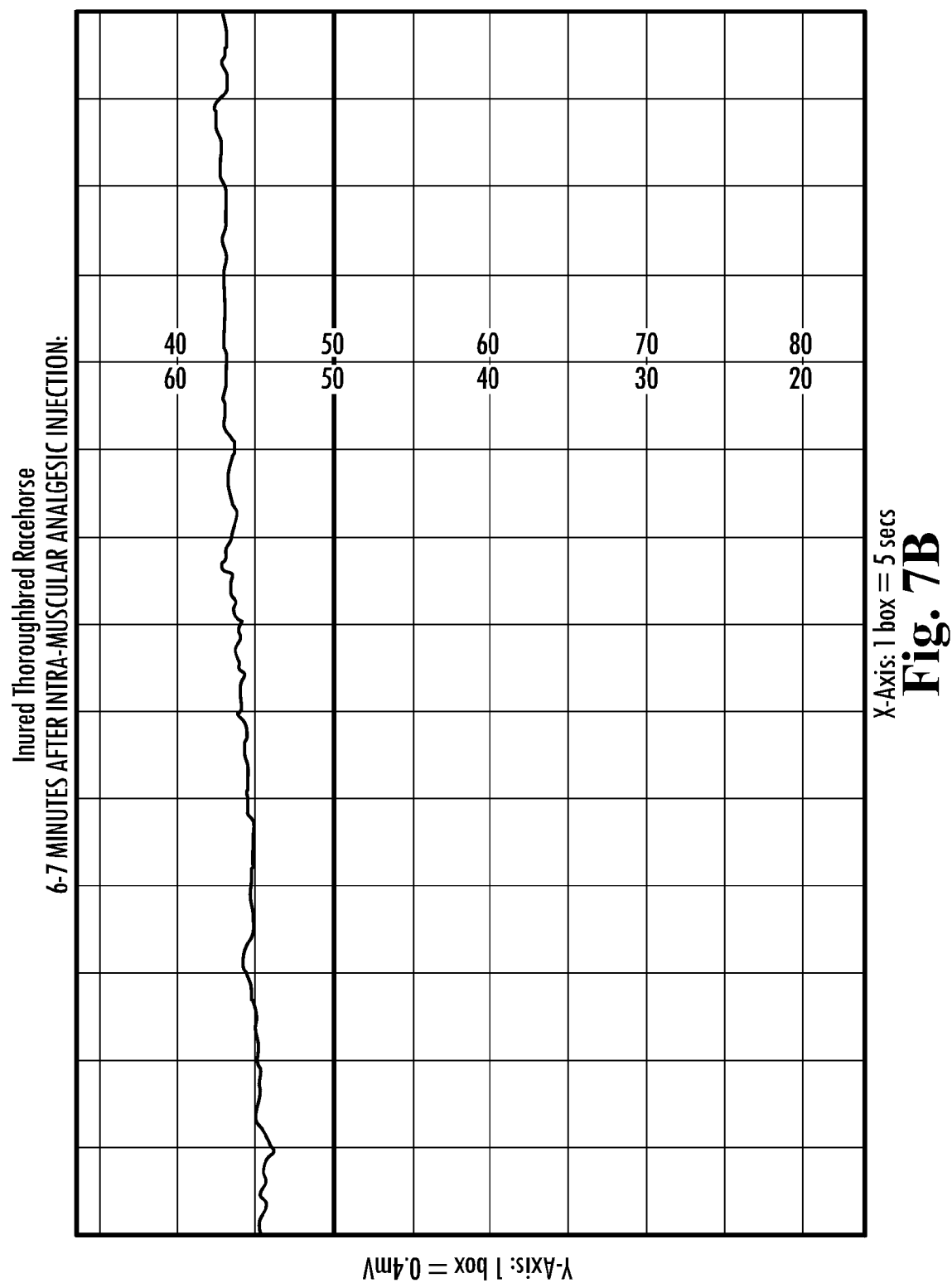
Figure 8A:
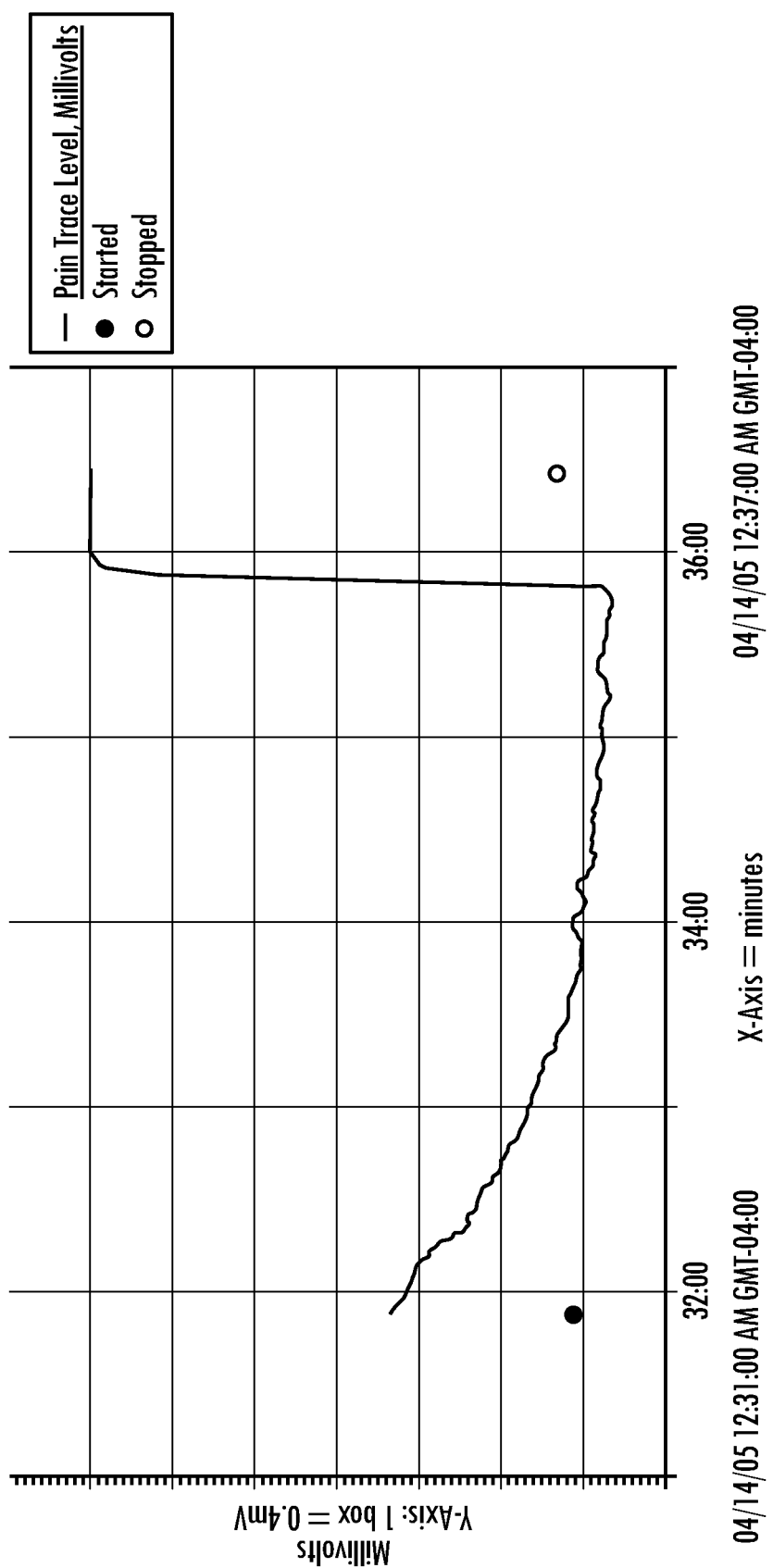
FIGS. 8a and b show the reading of a lame horse before and after healing (shown on computer generated graph).
Figure 8B:
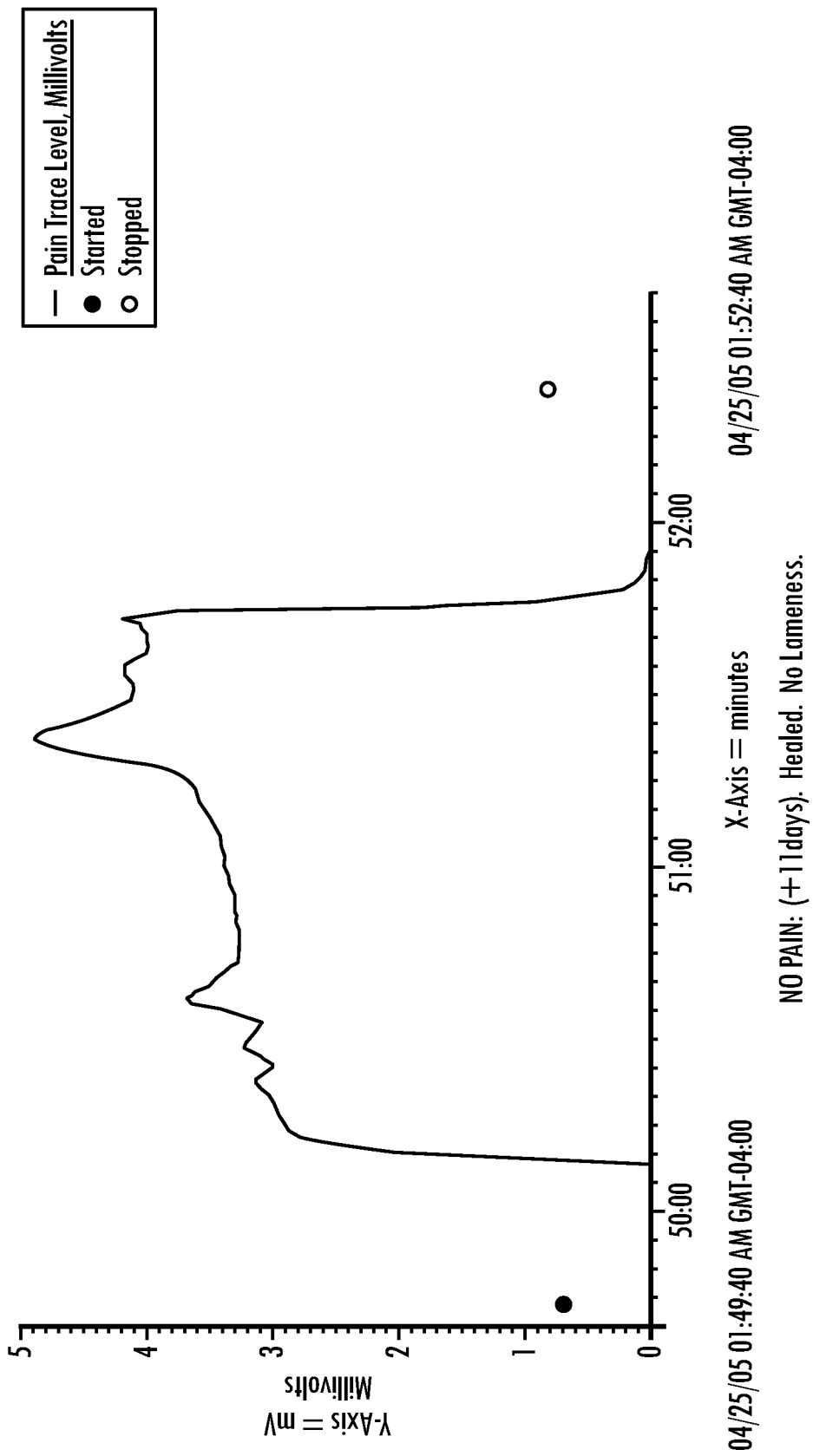

FIGS. 7a and b show pain and Pain Relief in Horses (shown on strip chart recorder). FIG. 7a shows a 2 year old female horse suffering post-surgical pain, before prescribed analgesic injection. FIG. 7b shows the same horse 6-7 minutes after prescribed analgesic injection. FIGS. 8a and b show a lame horse before and after healing (shown on computer generated graph). FIG. 8a shows a 3 year old lame male horse with swollen, cut foot. FIG. 8b shows the same horse one week later. Foot healed, lameness gone.

Example 6

Figure 9A:
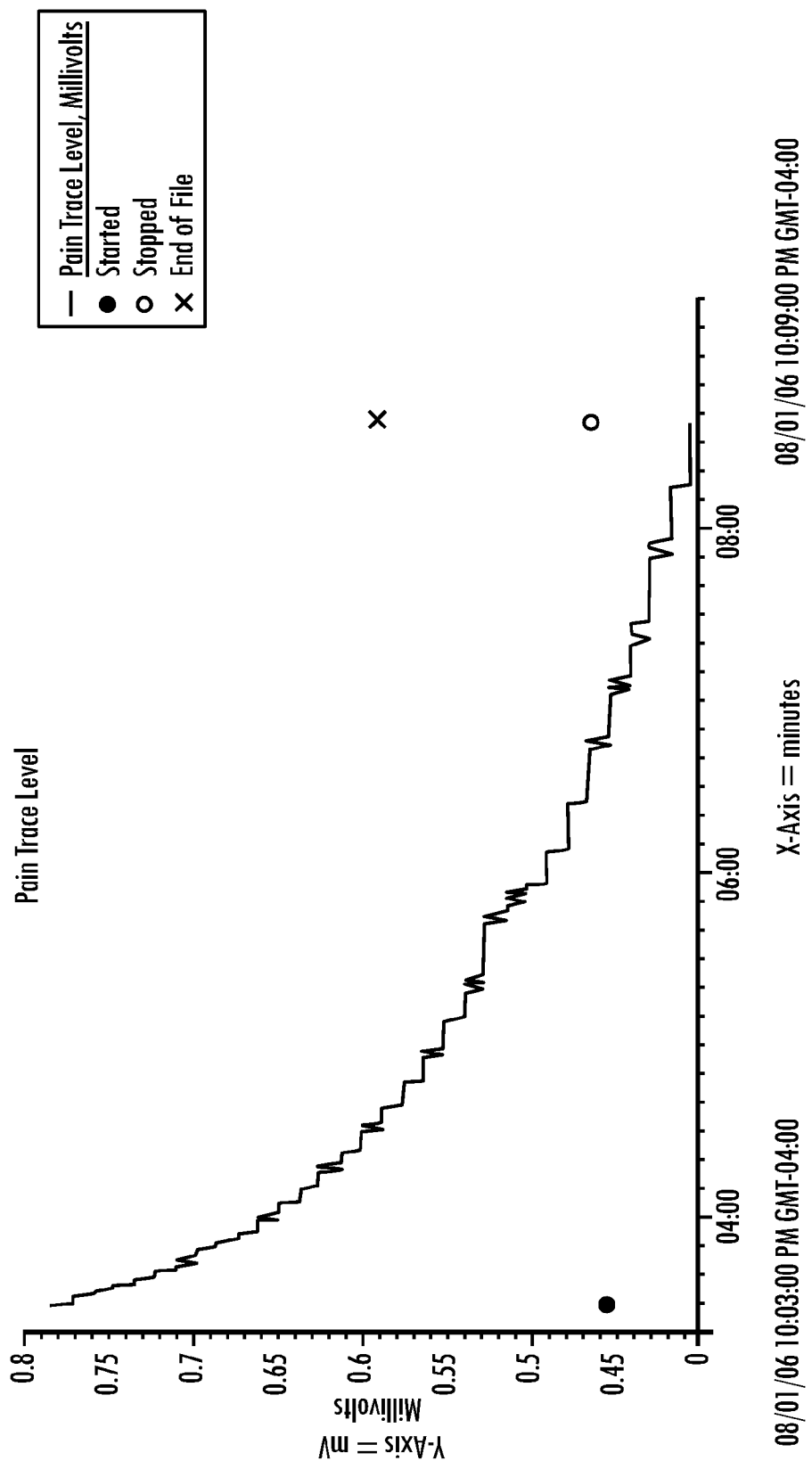
FIGS. 9a and b show sensor offset potentials only measured by pressing two gelled sensors together gel to gel and connecting them to a data gathering device.
Figure 9B:
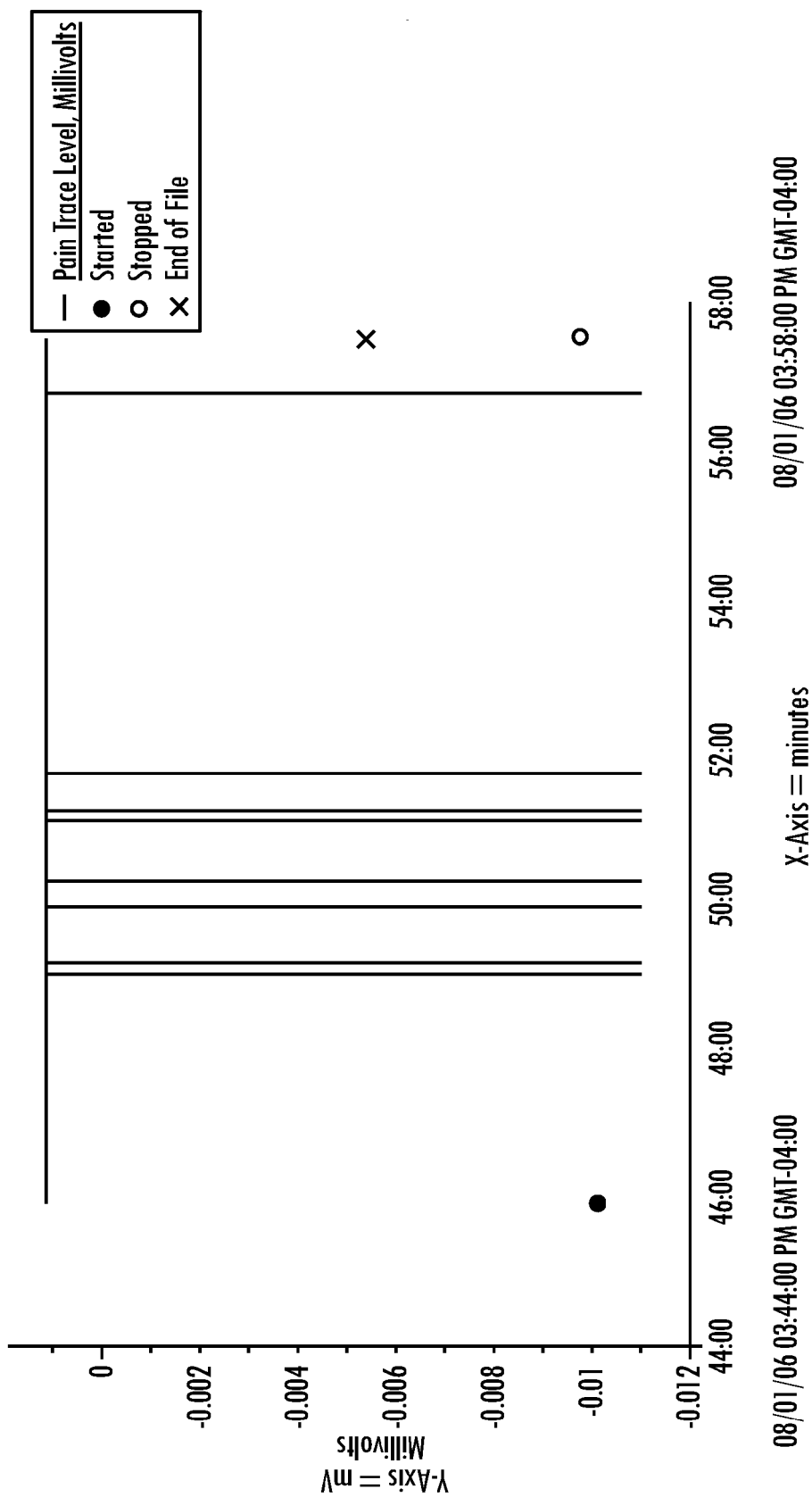

FIGS. 9a and b show pure offset potentials measured by pressing two sensor's sensing faces together and connecting them to the measuring device. There is no connection here to any subject. FIG. 9a shows that sensors with relatively high offset potential (0.75 mV) create their own, large traces which decay over time, adding a changing level of distortion to readings taken on any subject. Often this voltage potential can exceed the size of the voltage being measured in a subject. FIG. 9b shows that sensors with very low offset potential (0.01 mV) add only a minimal and unchanging distortion, which is much lower than the vast majority of two-sensor site readings from animal or human subjects.

Example 7

Figure 10A:
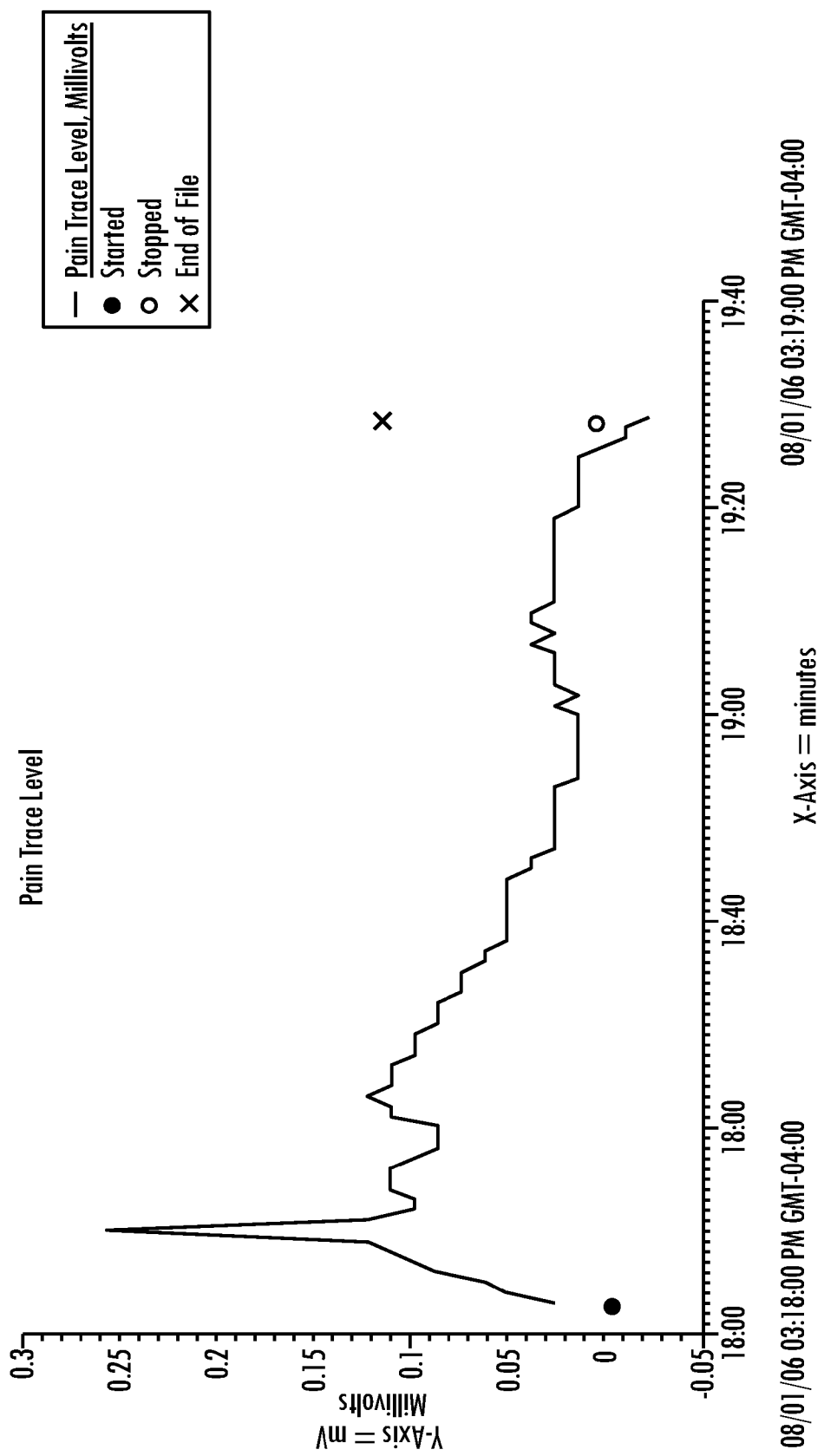
FIGS. 10a and b show the magnitude distortion of subject readings caused by electrodes with different amounts of offset potential.

FIGS. 10a and b show the distortion of subject readings caused by sensors with different amounts of offset potential. Subject: 51 year old male human with no pain.

Figure 10B:
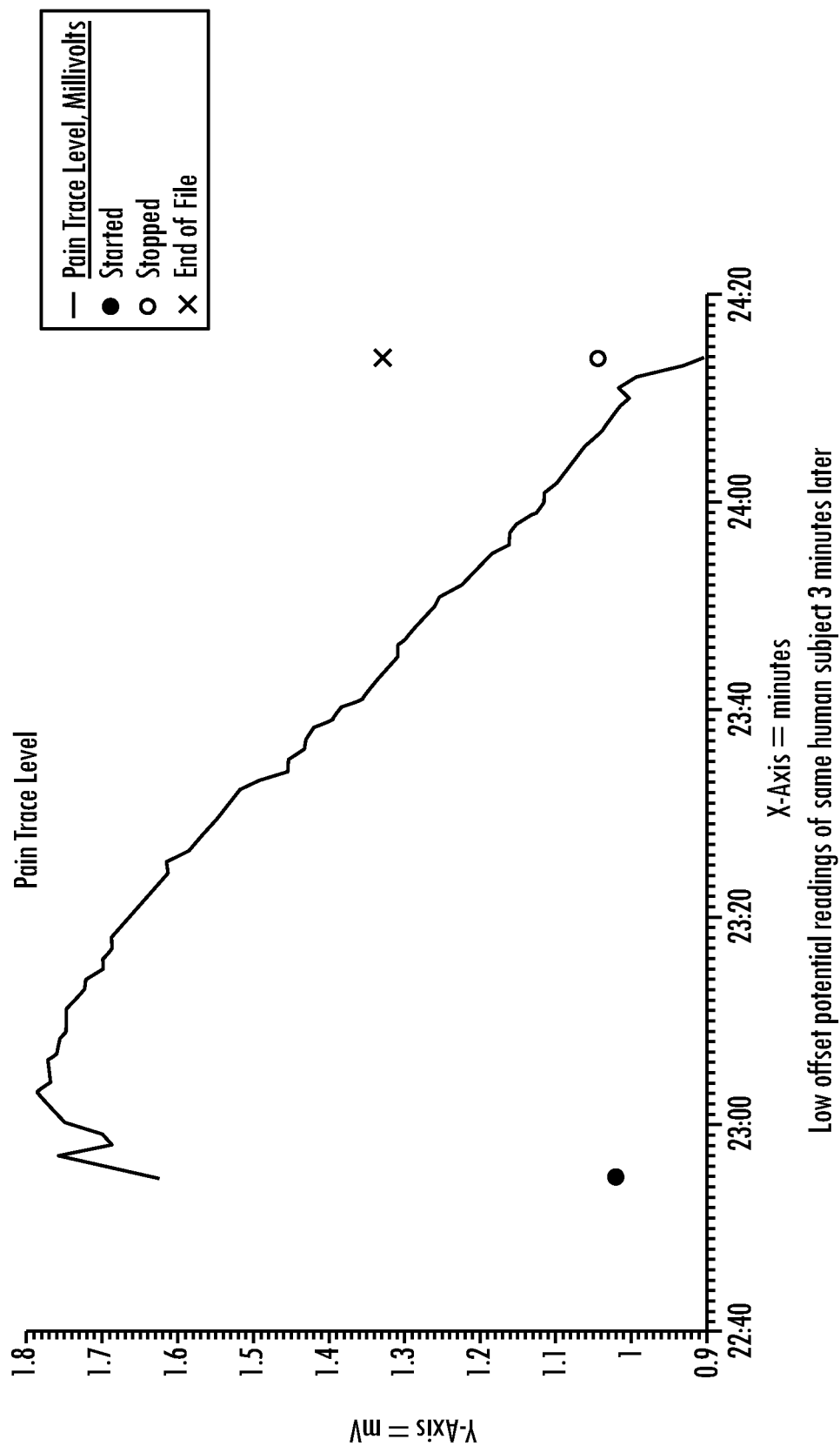

FIG. 10a shows a human subject in a non-pain state. The offset potential of the sensors used equals 0.01 mV. FIG. 10b shows the same human subject, 8 minutes later. The offset potential of the sensors used equals 5.0 mV. Note added distortion from high offset potential completely changes the nature of the reading obtained from subject.

Example 8

Figure 11A:
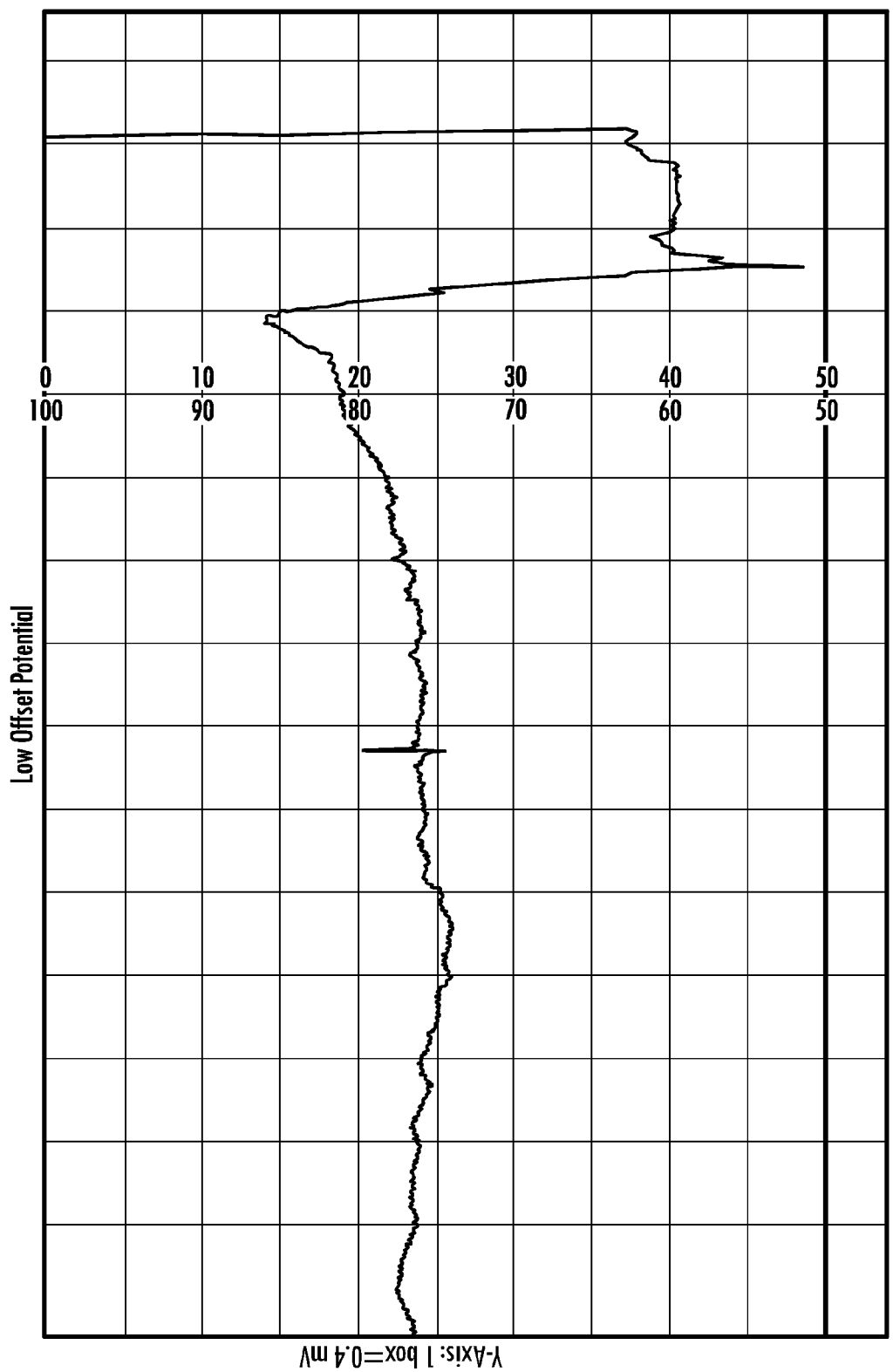
FIGS. 11a and b show the magnitude of the distortions of the sensors in the prior art.
Figure 11B:
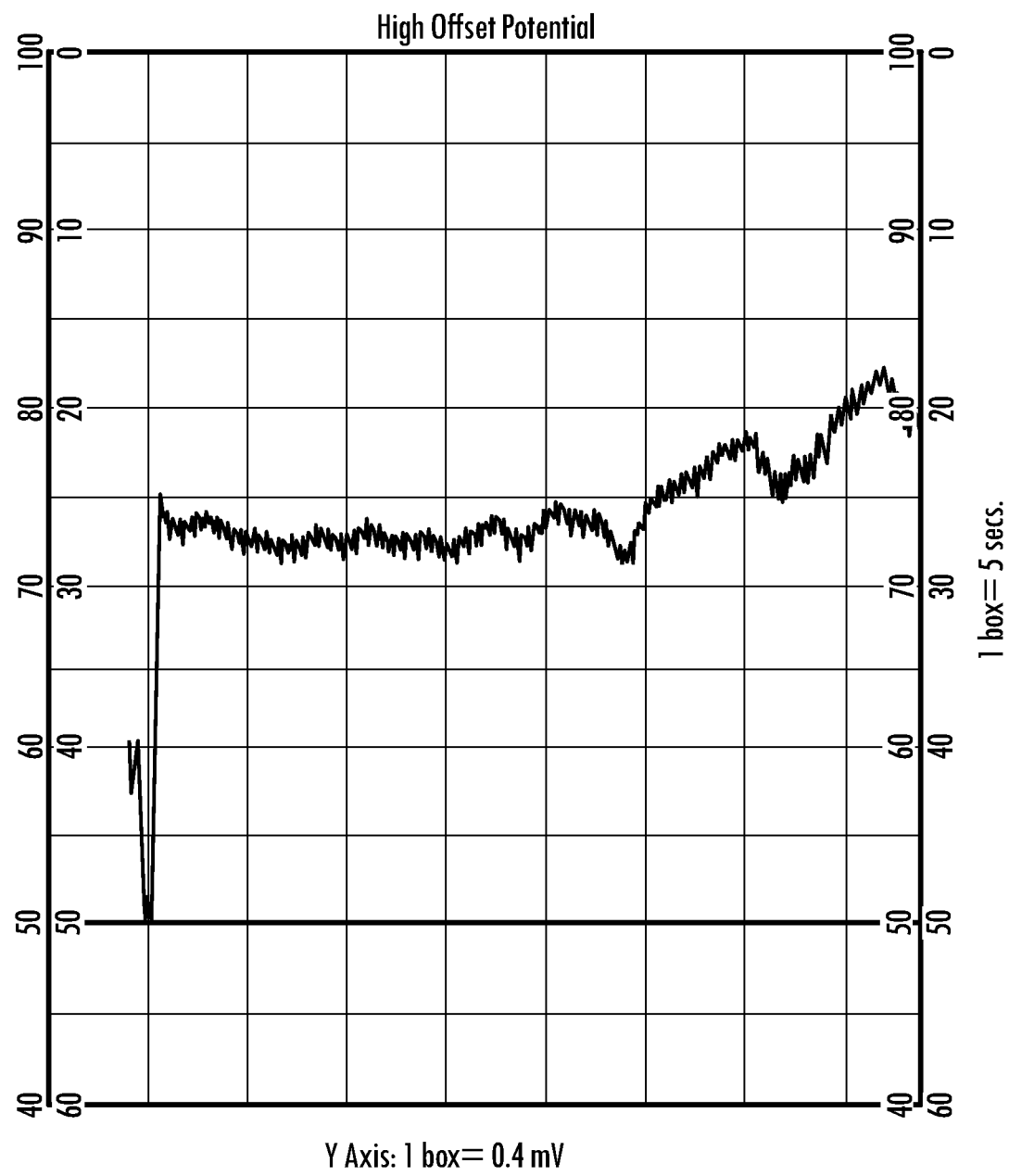

FIGS. 11a and b show the distortions of subject readings caused by sensors with different amounts of offset potential. Subject: 3 year old male horse with no known pain. FIG. 11a shows the horse in a non-pain state. The offset potential of the electrodes used equals 0.01 mV. FIG. 11b shows the same horse 8 minutes later. The offset potential of the electrodes used equals 4.2 mV. Note how the added distortion of the high offset potential here has even changed which side of the X=0 baseline the trace occurs on. In this case, this could have caused a pain-free state to be mistaken for a painful state.

Example 9

Figure 12A:
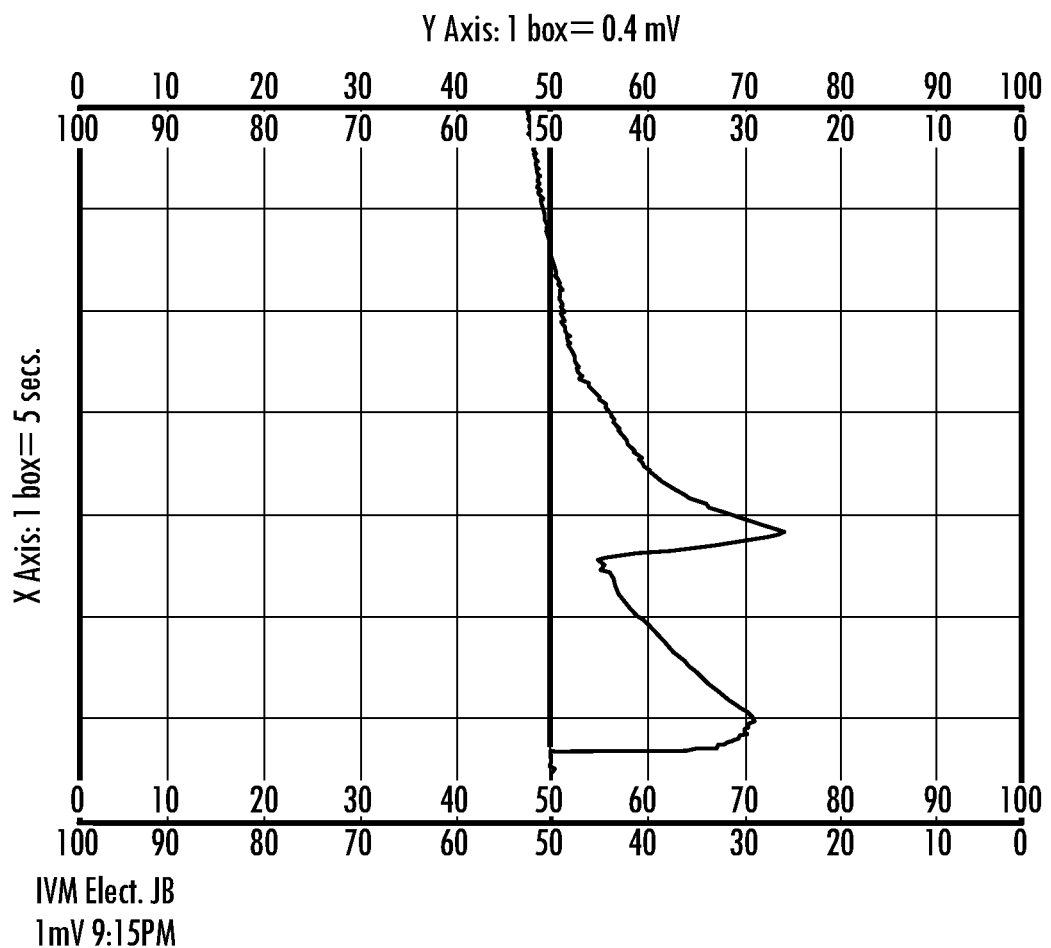
FIGS. 12a-d show the inconsistency in readings taken with reusable, cup-style, Ag+AgCl mixture sensors.
Figure 12B:
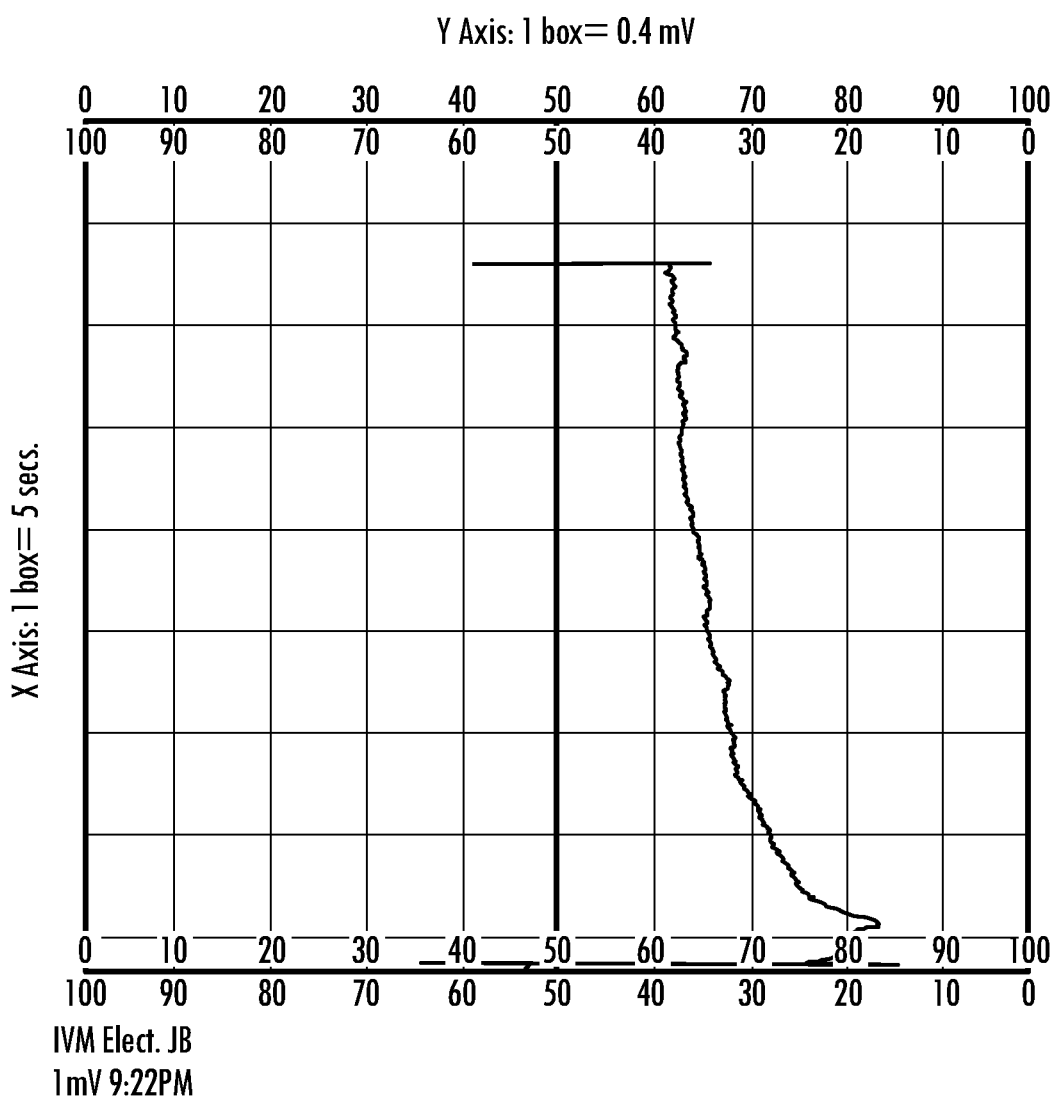
Figure 12C:
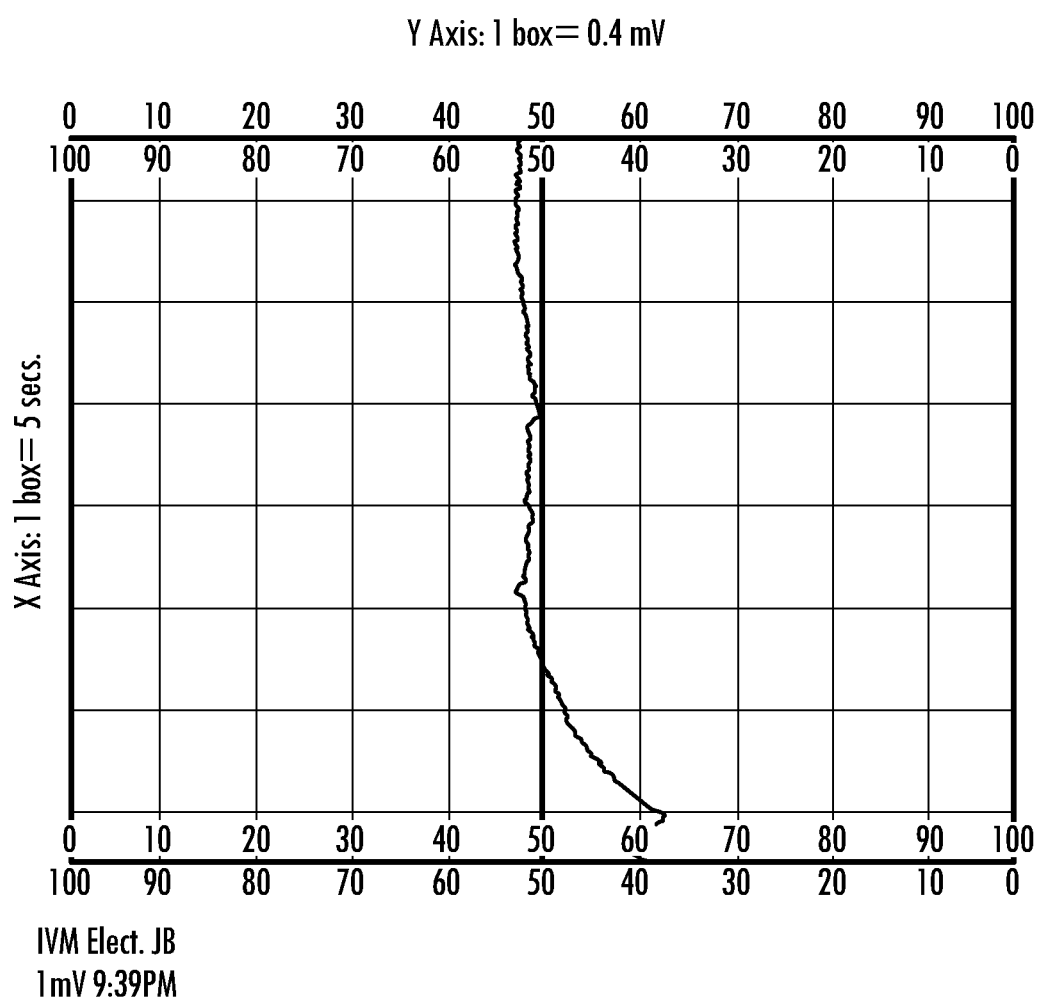
Figure 12D:
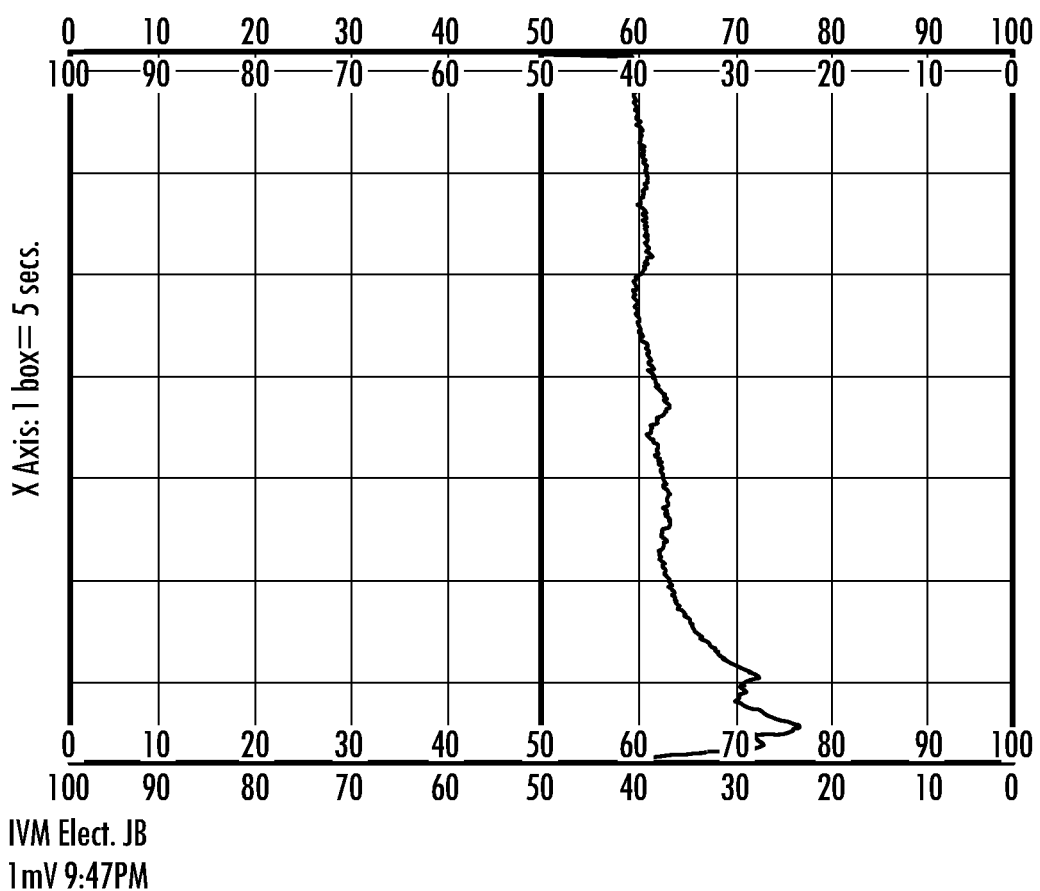
Figure 13A:
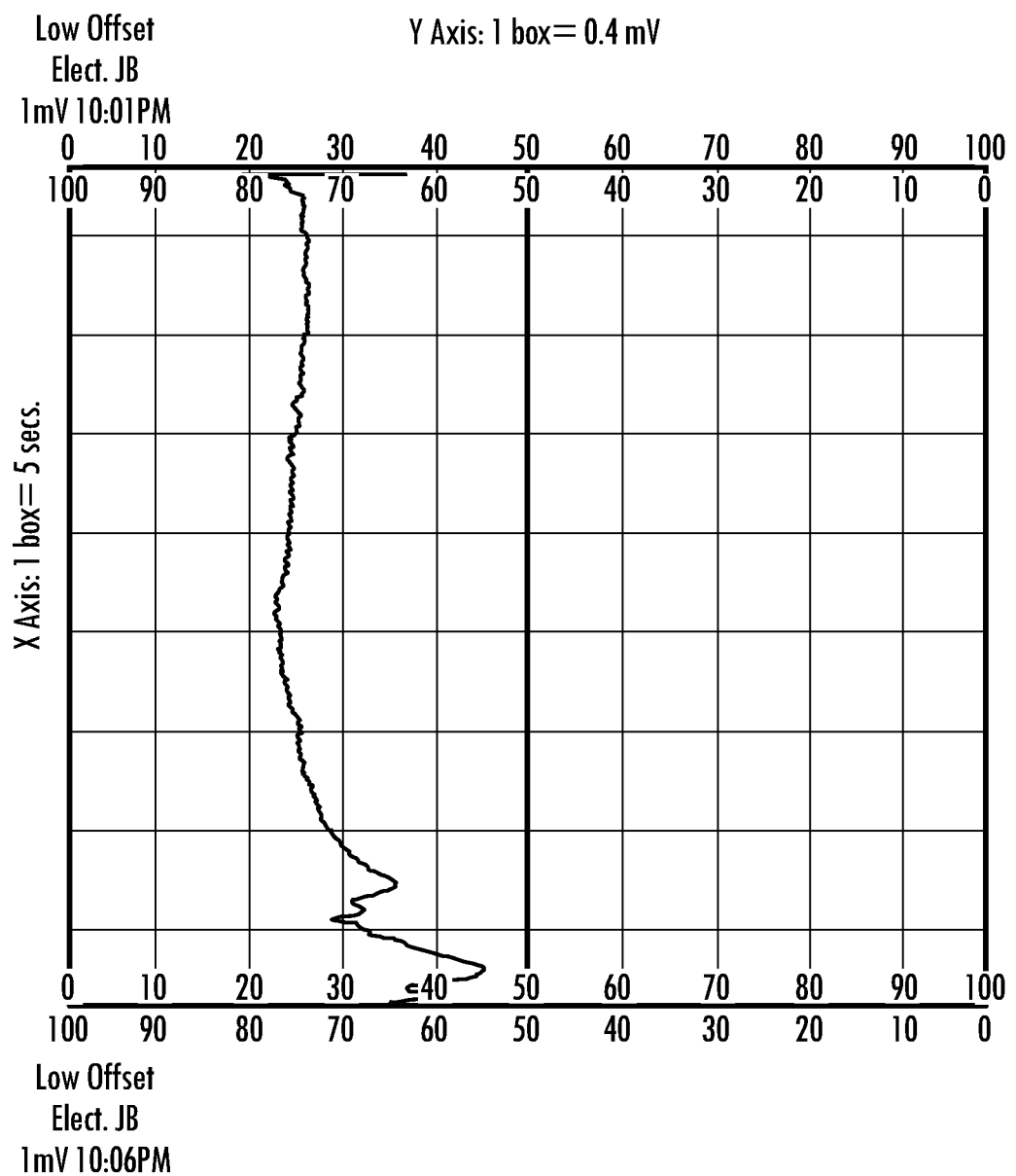
FIGS. 13a-d show the consistency in readings taken with the AgCl coated Silver sensors of the present invention.
Figure 13B:
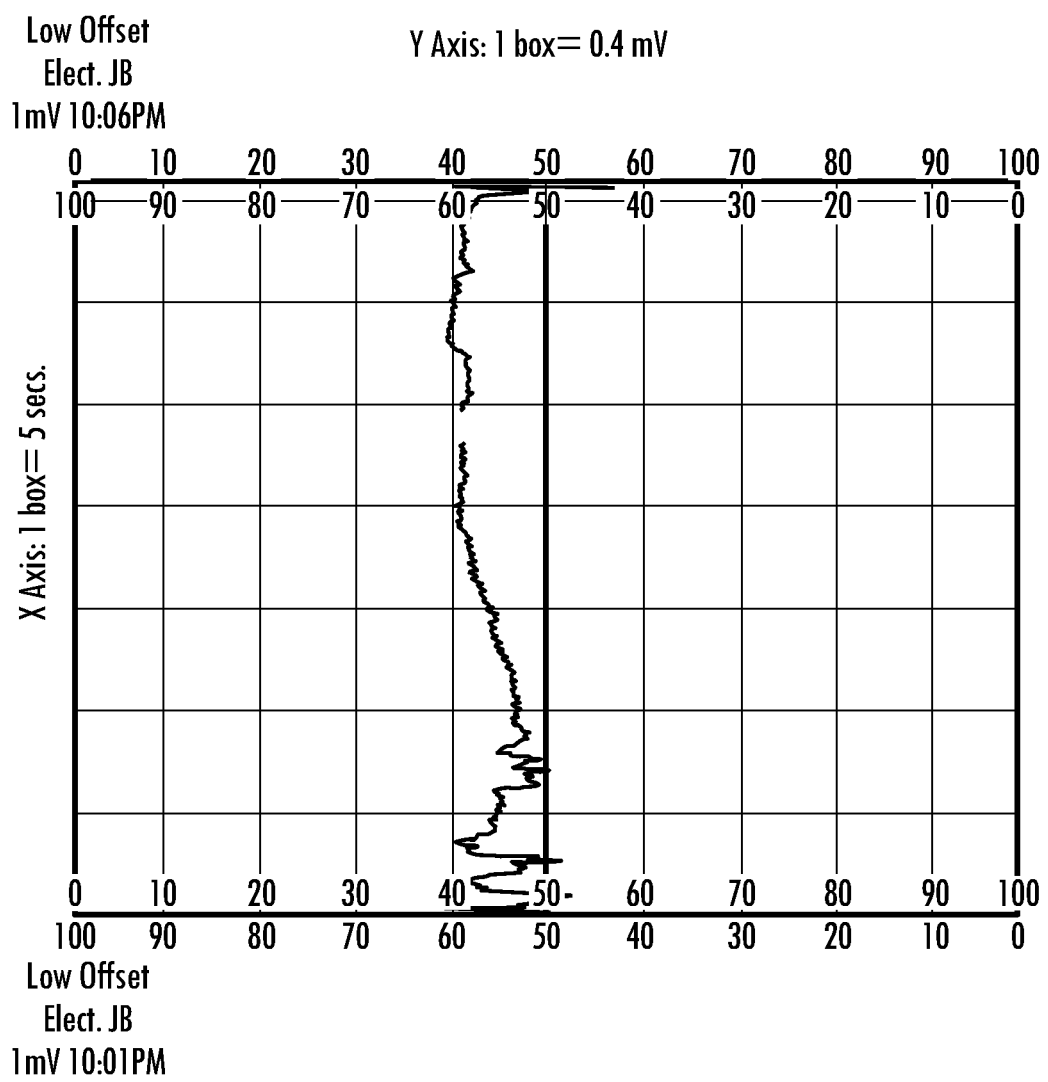
Figure 13C:
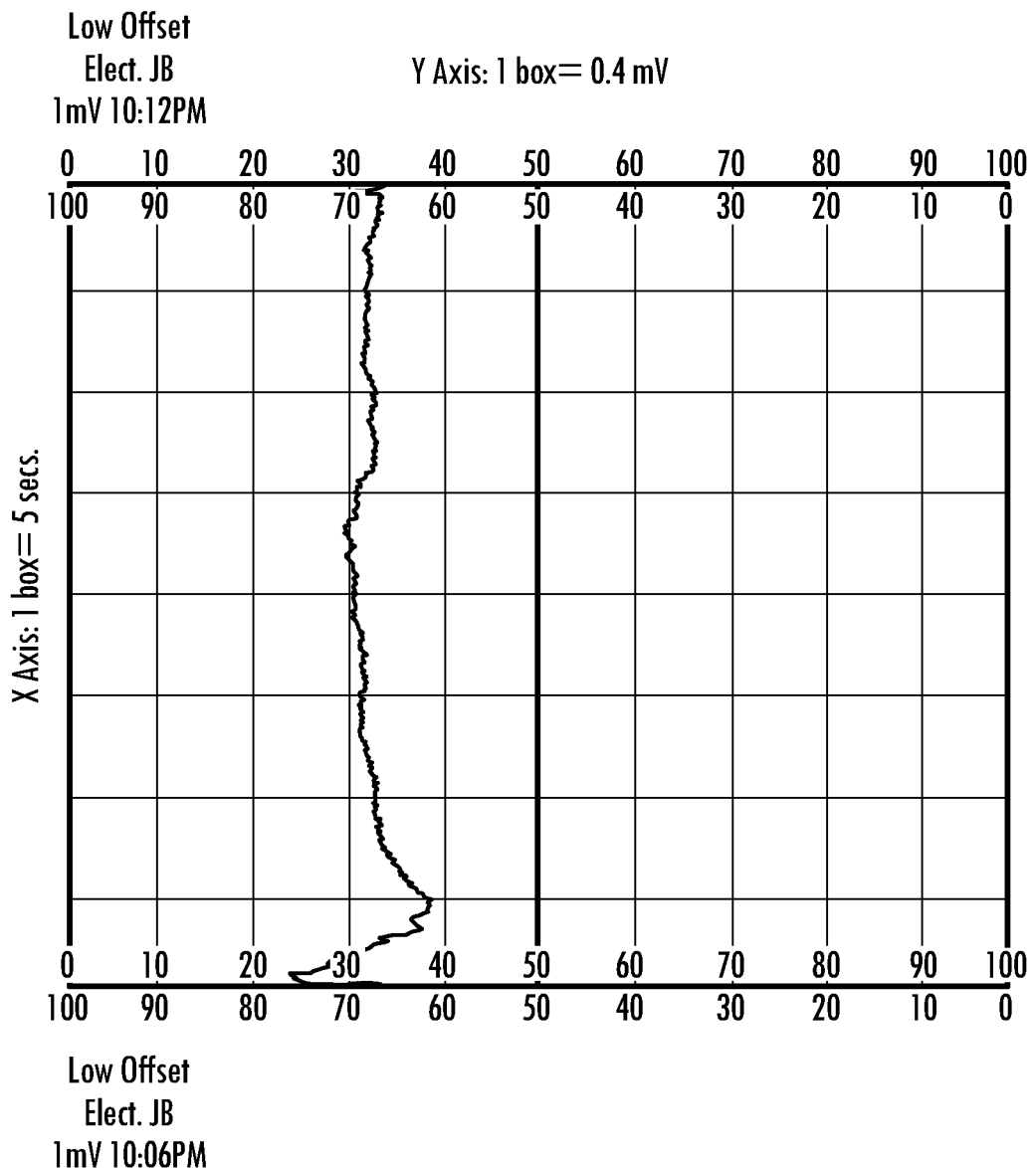
Figure 13D:
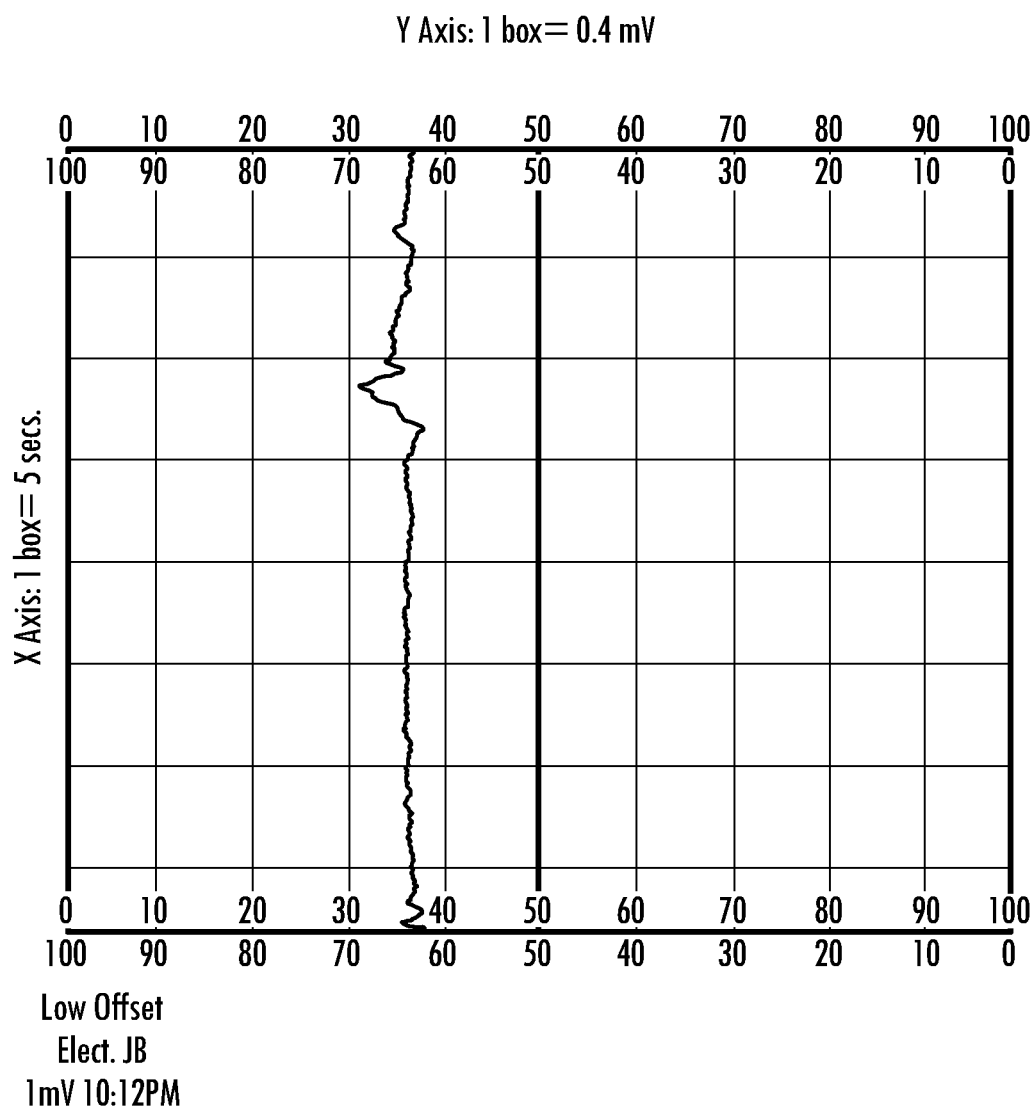

FIGS. 12a-d shows the inconsistency in four readings taken with reusable, cup-style, Ag+AgCl mixture sensors. All readings were taken on same subject just minutes apart (FIG. 12a, 9:15 P.M.; FIG. 12b, 9:22 P.M.; FIG. 12c 9:39 P.M.; FIG. 12d 9:47 P.M.). Note great variability. Subject was normal, healthy 54 year old white male, not in pain, and without ANS dysfunction of any kind. FIGS. 13a-d show the consistency in four readings taken with AgCl coated Ag sensors of the present method. All readings were taken on same subject as in FIGS. 12a-d, just minutes apart from one another (FIG. 13a, 9:54 P.M.; FIG. 13b, 10:01 P.M.; FIG. 13c 10:06P.M.; FIG. 13d 10:12 P.M.). Much greater consistency is observed in readings than among those in FIGS. 12a-d.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. An article of manufacture, to quantify nociception and pain comprising:
at least two self adhesive low offset sensors matched with each other to have offset potential between the matched pairs below about +/−0.01 mV and having an offset potential over a measuring time consistently below about +/−0.01 mV
said at least two self adhesive low offset sensors having a coating to conduct a difference in electrical potential caused by an activation of a sympathetic nerve and an activation of a parasympathetic nerve;
and a data gathering device connected to the sensors capable of measuring a voltage difference between the sensors caused by the activation of the sympathetic nerve and the activation of the parasympathetic nerve.

2. The article of claim 1, wherein the coating is an AgCl coating on a silver substrate.

3. The article of claim 1, wherein the coating is a pre-applied conductive gel disposed on a sensing side of the sensors.

4. The article of claim 1, wherein the sensors are connected to the data gathering device via lead wires across a resistor of 0.5 to 500 k-Ohms.

5. The article of claim 1, wherein the sensors are 10 mm in diameter.

6. The article of claim 1, wherein the sensors are disposable.

7. A device suitable for detecting a shift in the autonomic nervous system, comprising a first sensor and at least one other sensor,
   wherein said first sensor is matched with the at least one other sensor so that the offset potential of each matched pair is below about +/−0.01 mV over a measuring time; and
   the first sensor and the at least one other sensor having a coating to conduct a difference in electrical potential caused by an activation of a sympathetic nerve and an activation of a parasympathetic nerve; and
   a data gathering device connected to the sensors capable of measuring a voltage difference between the sensors caused by the activation of the sympathetic nerve and the activation of the parasympathetic nerve.

8. The device of claim 7, wherein the sensors have an exposed-to-gel sensing side of silver chloride coated silver.

9. The device of claim 7, wherein a conductive gel is pre-applied to the sensors.

10. The device of claim 7, wherein the sensors are about 10 mm in diameter.

11. The device of claim 7, wherein the sensors are disposable.

12. A method for detecting a shift in the autonomic nervous system, comprising the steps of:
   a) selecting at least two sensors having a paired offset potential over a measuring time consistently below about +/−0.01 mV;
   b) affixing the at least two selected sensors to contralateral sides of an animal or human; and
   c) measuring a voltage difference between said sensors to quantify a difference in electrical potential caused by an activation of a sympathetic nerve and an activation of a parasympathetic nerve.

13. The method of claim 12 wherein the voltage difference in step c is measured continuously.

14. The method of claim 12, wherein the voltage difference of step c is recorded, displayed or both recorded and displayed by a data gathering device.

15. The method of claim 12, wherein the voltage difference of step c) is correlated to a Visual Analogue Scale of self-reported pain.

16. The method of claim 12, further comprising a step of diagnosing conditions of altered ANS function.

17. The method of claim 12, further comprising a step of ascertaining the effectiveness of medicine.

18. The method of claim 12, wherein the sensors are affixed to a human.

19. The method of claim 12, wherein the sensors are affixed to an animal.

20. The method of claim 12, wherein at least one sensor is affixed to each hand of a human.

* * * * *